(12) United States Patent
Breault et al.

(10) Patent No.: US 6,632,820 B1
(45) Date of Patent: Oct. 14, 2003

(54) PYRIMIDINE COMPOUNDS

(75) Inventors: Gloria Anne Breault, Macclesfield (GB); Philip John Jewsbury, Macclesfield (GB); Janet Elizabeth Pease, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,681

(22) PCT Filed: Aug. 24, 1999

(86) PCT No.: PCT/GB99/02797

§ 371 (c)(1),
(2), (4) Date: Feb. 26, 2001

(87) PCT Pub. No.: WO00/12486

PCT Pub. Date: Mar. 9, 2000

(30) Foreign Application Priority Data

Aug. 29, 1998 (GB) ............................................. 9818987
Dec. 24, 1998 (GB) ............................................. 9828506

(51) Int. Cl.$^7$ ..................... C07D 239/48; A61K 31/505
(52) U.S. Cl. ..................... 514/256; 544/326; 544/327; 544/328; 544/329
(58) Field of Search ................... 544/326, 327, 544/328, 329; 514/256

(56) References Cited

U.S. PATENT DOCUMENTS

| | | | |
|---|---|---|---|
| 4,983,608 A | 1/1991 | Effland et al. | 514/256 |
| 5,516,775 A | 5/1996 | Zimmermann et al. | 514/224.2 |
| 5,610,303 A | 3/1997 | Kimura et al. | 544/326 |
| 5,739,143 A | 4/1998 | Adams et al. | 514/275 |
| 5,859,041 A | 1/1999 | Liverton et al. | 514/396 |

FOREIGN PATENT DOCUMENTS

| | | |
|---|---|---|
| CA | 2231765 | 9/1998 |
| EP | 0 363 002 | 4/1990 |
| EP | 0 379 806 B1 | 8/1990 |
| EP | 0 945 443 A1 | 9/1999 |
| WO | WO 91/18887 | 12/1991 |
| WO | WO 92/20642 | 11/1992 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/15952 | 6/1995 |
| WO | WO 96/05177 | 2/1996 |
| WO | WO 96/28427 | 9/1996 |
| WO | WO 96/40143 | 12/1996 |
| WO | WO 97/19065 | 5/1997 |
| WO | WO 97/35856 | 10/1997 |
| WO | WO 97/47618 | 12/1997 |
| WO | WO 98/11095 | 3/1998 |
| WO | WO 98/16230 | 4/1998 |
| WO | WO 98/18782 | 5/1998 |
| WO | WO 98/25619 | 6/1998 |
| WO | WO 98/33798 | 8/1998 |
| WO | WO 98/41512 | 9/1998 |
| WO | WO 98/54093 | 12/1998 |
| WO | WO 98/56788 | 12/1998 |
| WO | WO 99/01136 | 1/1999 |
| WO | WO 99/32121 | 1/1999 |
| WO | WO 99/18942 | 4/1999 |

(List continued on next page.)

OTHER PUBLICATIONS

El–Kerdawy et al.; 2,4–Bis(Substituted)–5–Nitropyrimidines of Expected Diuretic Action; Egypt J. Chem. vol. 29, No. 2, 1986, pp. 247–251.
Fiziol Akt Veshchestva, 1975, vol. 7, pp. 68–72.
Ghosh et al.; 2,4–Bis(arylamino)–5–methylpyrimidines as Antimicrobial Agents;; J. Med. Chem., 1967, vol. 10, No. 5, pp. 974–975.
Ghosh, 2,4–Bis(Arylamino)–6–Methyl Pyrimidines as Antimicrobial Agents, J. Indian Chem. Soc., vol. 58, No. 5, 1981, pp. 512–513.
Ghosh, 2,4–Bis(arylamino)–6–methylpyrimidines as an antimicrobial agents, Chemical Abstract No. 97712f, vol. 95, 1981, pp. 648.
Schmidt et al.; "A Convenient Synthesis of 2–substituted 4–Amino–5–pyrimidinecarbonitriles"; J. Heterocycle Chem., 1997, vol. 24, No. 5, pp. 1305–1307.

*Primary Examiner*—Deepak Rao
(74) *Attorney, Agent, or Firm*—Morgan, Lewis & Bockius LLP

(57) ABSTRACT

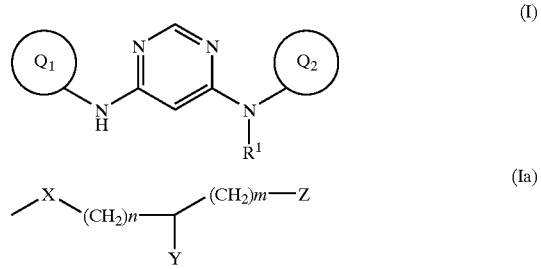

A pyrimidine derivative of formula (I) wherein, for example, $R^1$ is-(1–6C)alkyl or (3–5C)alkenyl [optionally substituted by a phenyl substituent]; $Q_1$ and $Q_2$ are independently selected from phenyl, naphthyl, indanyl and 1,2,3,4-tetrahydronaphthyl; and one or both of $Q_1$ and $Q_2$ bears one substituent of formula (Ia) [provided that when present in $Q_1$ the substituent of formula (Ia) is not adjacent to the —NH-link]; wherein, for example, X is $CH_2$, O, S or NH; Y is H or as defined for Z; Z is OH, SH, $NH_2$, (1–4C)alkoxy, (1–4C)alkylthio, —NH(1–4C)alkyl, —N[(1–4C)alkyl]$_2$ or —NH-(3–8C)cycloalkyl; n is 1, 2 or 3; m is 1, 2 or 3; and $Q_1$ and $Q_2$ may each optionally bear other substituents selected from halogeno, (1–6C)alkyl, cyano and (2–4C)alkenyl, or a pharmaceutically-acceptable salt, or in-vivo-hydrolysable ester thereof; are useful as anti-cancer agents; and processes for their manufacture and pharmaceutical compositions containing them are described.

11 Claims, No Drawings

FOREIGN PATENT DOCUMENTS

| | | |
|---|---|---|
| WO | WO 99/31073 | 6/1999 |
| WO | WO 99/50250 | 10/1999 |
| WO | WO 00/12485 | 3/2000 |
| WO | WO 00/17202 | 3/2000 |
| WO | WO 00/17203 | 3/2000 |
| WO | WO 00/25780 | 5/2000 |
| WO | WO 00/26209 | 5/2000 |
| WO | WO 00/44750 | 8/2000 |
| WO | WO 00/49018 | 8/2000 |
| WO | WO 00/53595 | 9/2000 |
| WO | WO 00/55161 | 9/2000 |
| WO | WO 00/59892 | 10/2000 |
| WO | WO 00/78731 A1 | 12/2000 |
| WO | WO 01/14375 | 3/2001 |
| WO | WO 01/29009 A1 | 4/2001 |
| WO | WO 01/30778 A1 | 5/2001 |
| WO | WO 01/64653 A1 | 9/2001 |
| WO | WO 01/64654 A1 | 9/2001 |
| WO | WO 01/64655 A1 | 9/2001 |
| WO | WO 01/64656 A1 | 9/2001 |

PYRIMIDINE COMPOUNDS

This application is the national phase of international application PCT/GB99/02797 filed Aug. 24, 1999 which designated the U.S.

The invention relates to pyrimidine derivatives, or pharmaceutically-acceptable salts or in-vivo-hydrolysable esters thereof, which possess anti-cell proliferative (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments for use in the production of an anti-cell proliferation (anti-cancer) effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain 4,6-pyrimidine compounds surprisingly inhibit the effects of cell cycle kinases showing selectivity for CDK2, CDK4 and CDK6, and thus possess anti-cancer (anti-cell proliferation) properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I)

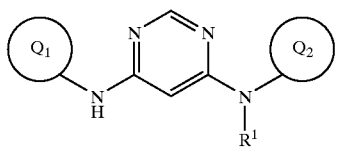

(I)

wherein
$R^1$ is selected from (1–6C)alkyl [optionally substituted by one or two substituents independently selected from halo, amino, (1–4C)alkylamino, di-[(1–4C)alkyl] amino, hydroxy, cyano, (1–4C)alkoxy, (1–4C) alkoxycarbonyl, carbamoyl, —NHCO(1–4C)alkyl, trifluoromethyl, phenylthio, phenoxy, pyridyl, morpholino], benzyl, 2-phenylethyl, (3–5C)alkenyl [optionally substituted by up to three halo substituents, or by one trifluoromethyl substituent, or one phenyl substituent], N-phthalimido-(1–4C)alkyl, (3–5C) alkynyl [optionally substituted by one phenyl substituent] and (3–6C)cycloalkyl-(1–6C)alkyl;

wherein any phenyl or benzyl group in $R^1$ is optionally substituted by up to three substituents independently selected from halogeno, hydroxy, nitro, amino, (1–3C) alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C) alkyl]amino, hydroxy and trifluoromethyl], (3–5C) alkenyl [optionally substituted by up to three halo substituents, or by one trifluoromethyl substituent], (3–5C)alkynyl, (1–3C)alkoxy, —SH, —S-(1–3 C)alkyl, carboxy, (1–3 C)alkoxycarbonyl;

$Q_1$ and $Q_2$ are independently selected from phenyl, naphthyl, indanyl and 1,2,3,4-tetrahydronaphthyl;

and one or both of $Q_1$ and $Q_2$ bears on any available carbon atom one substituent of the formula (Ia) and $Q_2$ may optionally bear on any available carbon atom further substituents of the formula (Ia)

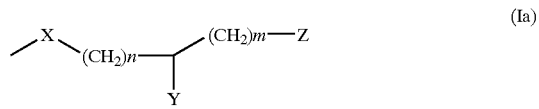

(Ia)

[provided that when present in $Q_1$ the substituent of formula (Ia) is not adjacent to the —NH— link];

wherein
X is $CH_2$, O, S, NH or NRx [wherein Rx is (1–4C) alkyl, optionally substituted by one substituent selected from halo, amino, cyano, (1–4C)alkoxy or hydroxy];

Y is H or as defined for Z; Z is OH, SH, $NH_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C) alkyl or (1–4C)alkanoyl], morpholino or thiomorpholino; n is 1, 2 or 3; m is 1, 2 or 3;

and $Q_1$ and $Q_2$ may each optionally and independently bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino-(1–3C)alkyl, (1–4C) alkylamino-(1–3C)alkyl, di-[(1–4C)alkyl]amino-(1–3C)alkyl, cyano-(1–4C)alkyl, (2–4C) alkanoyloxy-(1–4C)-alkyl, (1–4C)alkoxy-(1–3C) alkyl, carboxy-(1–4C)alkyl, (1–4C)alkoxycarbonyl-(1–4C)alkyl, carbamoyl-(1–4C)alkyl, N-(1–4C) alkylcarbamoyl-(1–4C)alkyl, N,N-di-[(1–4C)alkyl]-carbarmoyl-(1–4C)alkyl, pyrrolidin-1-yl-(1–3 C)alkyl, piperidin-1-yl-(1–3C)alkyl, piperazin-1-yl-(1–3C)alkyl, morpholino-(1–3 C)alkyl, thiomorpholino-(1–3C)alkyl, piperazin-1-yl, morpholino, thiomorpholino, (1–4C)alkoxy, cyano-(1–4C)alkoxy, carbamoyl-(1–4C)alkoxy, N-(1–4C)alkylcarbarnoyl-(1–4C)alkoxy, N,N-di-[(1–4C)alkyl]-carbarmoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido (H$_2$N—CO—NH—), (1–4C)alkylNH—CO—NH—, di-[(1–4C)alkyl]-N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or where appropriate in addition to, the above optional substituents, Q$_1$ and/or Q$_2$ may optionally bear on any available carbon atom up to two further substituents independently selected from (3–8C)cycloalkyl, phenyl-(1–4C)alkyl, phenyl-(1–4C)alkoxy, phenylthio, phenyl, naphtnyl, benzoyl, phenoxy, benzimidazol-2-yl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C)alkoxy substituents may optionally bear up to five substituents independently selected from halogeno, (1–4C)alkyl and (1–4C)alkoxy; or a pharmaceutically-acceptable salt or in-vivo-hydrolysable ester thereof.

A suitable value for a ring substituent when it is a 5- or 6-membered aromatic heterocycle (linked via a ring carbon atom and containing one to three heteroatoms independently selected from oxygen, sulphur and nitrogen) is, for example, pyrrole, furan, thiophene, imidazole, oxazole, isoxazole, thiazole, pyridyl, pyridazinyl, pyrimidinyl, pyrazinyl or p-isoxazine.

In this specification the term "alkyl" includes both straight and branched chain alkyl groups but references to individual alkyl groups such as "propyl" are specific for the straight chain version only. An analogous convention applies to other generic terms.

Suitable values for the generic radicals (such as in R$^1$ and in substituents on Q$_1$ and Q$_2$) referred to above include those set out below:

when it is halogeno is, for example, fluoro, chloro, bromo and iodo; (2–4C)alkenyl is, for example, vinyl and allyl; when it is (3–5C)alkenyl is, for example, allyl or buten-3-yl; when it is (3–5C)alkynyl is, for example, propyn-2-yl; when it is (2–4C)alkynyl is, for example, ethynyl and propyn-2-yl; when it is (3–6C)cycloalkyl-(1–6C)alkyl is, for example, cyclopropylmethyl; when it is (3–8C)cycloalkyl is, for example, cyclobutyl, cyclopentyl or cyclohexyl; when it is (1–4C)alkanoyl or (1–5C)alkanoyl is, for example, formyl and acetyl; when it is (1–4C)alkoxycarbonyl is, for example, methoxycarbonyl, ethoxycarbonyl, propoxycarbonyl and tert-butoxycarbonyl; when it is (1–3C)alkyl is, for example, methyl, ethyl, propyl, isopropyl; when it is (1–4C)alkyl is, for example, methyl, ethyl, propyl, isopropyl, butyl, isobutyl, sec-butyl or tert-butyl; when it is (1–6C)alkyl is, for example, methyl, ethyl, propyl, isopropyl, butyl, isobutyl, sec-butyl, tert-butyl or 3-methylbutyl or hexyl; when it is hydroxy-(1–3C)alkyl is, for example, hydroxymethyl, 1-hydroxyethyl, 2-hydroxyethyl and 3-hydroxypropyl; when it is hydroxy-(2–4C)alkyl is, for example, 2-hydroxyethyl and 3-hydroxypropyl; when it is fluoro-(1–4C)alkyl is, for example, fluoromethyl, difluoromethyl, trifluoromethyl and 2-fluoroethyl; when it is amino-(1–3C)alkyl is, for example, aminomethyl, 1-aminoethyl and 2-aminoethyl; when it is (1–4C)alkylamino-(1–3C)-alkyl is, for example, methylaminomethyl, ethylaminomethyl, 1-methylaminoethyl, 2-methylaminoethyl, 2-ethylamimoethyl and 3-methylaminopropyl; when it is di-[(1–4C)alkyl]amino-(1–3C)alkyl is, for example, dimethylaminomethyl, diethylaminomethyl, 1-dimethylaminomethyl, 2-dimethylaminomethyl and 3-dimethylaminopropyl; when it is cyano-(1–4C)alkyl is, for example cyanomethyl, 2-cyanoethyl and 3-cyanopropyl; when it is (2–4C)alkanoyloxy-(1–4C)-alkyl is, for example, acetoxymethyl, propionyloxymethyl, butyryloxymethyl, 2-acetoxyethyl and 3-acetoxypropyl; when it is (1–4C)alkoxy-(1–3C)alkyl is, for example, methoxymethyl, ethoxymethyl, 1-methoxyethyl, 2-methoxyethyl, 2-ethoxyethyl and 3-methoxypropyl; when it is carboxy-(1–4C)alkyl is, for example carboxymethyl, 1-carboxyethyl, 2-carboxyethyl and 3-carboxypropyl; when it is (1–4C)alkoxycarbonyl-(1–4C)alkyl is, for example, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; when it is carbamoyl-(1–4C)alkyl is, for example carbamoylmethyl, 1-carbamoylethyl, 2-carbamoylethyl and 3-carbamoylpropyl; when it is N-(1–4C)alkylcarbamoyl-(1–4C)alkyl is, for example, N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

when it is N,N-di-[(1–4C)alkyl]-carbamoyl-(1–4C)alkyl is, for example, N,N-dimethylcarbamoylmethyl, N-ethyl-N-methylcarbamoylmethyl, N,N-diethylcarbamoylmethyl, 1-(N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; when it is pyrrolidin-1-yl-(1–3C)alkyl is, for example, pyrrolidin-1-ylmethyl and 2-pyrrolidin-1-ylethyl; when it is piperidin-1-yl-(1–3C)alkyl is, for example, piperidin-1-ylmethyl and 2-piperidin-1-ylethyl; when it is piperazin-1-yl-(1–3C)alkyl is, for example, piperazin-1-ylmethyl and 2-piperazin-1-ylethyl; when it is morpholino-(1–3C)alkyl is, for example, morpholinomethyl and 2-morpholinoethyl; when it is thiomorpholino-(1–3C)alkyl is, for example, thiomorpholinomethyl and 2-thiomorpholinoethyl; when it is (1–4C)alkoxy is, for example, methoxy, ethoxy, propoxy, isopropoxy or butoxy; when it is cyano-(1–4C)alkoxy is, for example, cyanomethoxy, 1-cyanoethoxy, 2-cyanoethoxy and 3-cyanopropoxy; when it is carbamoyl-(1–4C)alkoxy is, for example, carbamoylmethoxy, 1-carbamoylethoxy, 2-carbamoylethoxy and 3-carbamoylpropoxy; when it is N-(1–4C)alkylcarbamoyl-(1–4C)alkoxy is, N-methylcarbamoylmethoxy, N-ethylcarbamoylmethoxy, 2-(N-methylcarbamoyl)ethoxy, 2-(N-ethylcarbamoyl) ethoxy and 3-(N-methylcarbarmoyl)propoxy; when it is N,N-di-[(1–4C)alkyl]-carbamoyl-(1–4C)alkoxy is, for example, N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl) propoxy; when it is 2-(1–4C)alkylaminoethoxy is, for example, 2-(methylamino)ethoxy, 2-(ethylamino)ethoxy and 2-(propylamino)ethoxy; when it is 2-di-[(1–4C)alkyl] aminoethoxy is, for example, 2-(dimethylamino)ethoxy, 2-(N-ethyl-N-methylamino)ethoxy, 2-(diethylamino)ethoxy and 2-(dipropylamino)ethoxy; when it is (1–4C) alkoxycarbonyl-(1–4C)alkoxy is, for example, methoxycarbonylmethoxy, ethoxycarbonylmethoxy, 1-methoxycarbonylethoxy, 2-methoxycarbonylethoxy, 2-ethoxycarbonylethoxy and 3-methoxycarbonylpropoxy; when it is halogeno-(1–4C)alkoxy is, for example, difluoromethoxy, trifluoromethoxy, 2-fluoroethoxy, 2-chloroethoxy, 2-bromoethoxy, 3-fluoropropoxy, 3-chloropropoxy and 2-chloro-2,1,1-trifluoroethoxy; when it is (2–4C)alkanoyloxy-(2–4C)alkoxy is, for example, 2-acetoxyethoxy, 2-propionyloxyethoxy, 2-butyryloxyethoxy and 3-acetoxypropoxy; when it is 2-(1–4C)alkoxyethoxy is, for example, 2-methoxyethoxy, 2-ethoxyethoxy; when it is carboxy-(1–4C)alkoxy is, for example, carboxymethoxy, 1-carboxyethoxy, 2-carboxyethoxy and 3-carboxypropoxy; when it is (3–5C) alkenyloxy is, for example, allyloxy; when it is (3–5C) alkynyloxy is, for example, propynyloxy; when it is (1–4C) alkylthio is, for example, methylthio, ethylthio or propylthio; when it is (1–4C)alkyylsulphinyl is, for example, methylsulphinyl, ethylsulphinyl or propylsulphinyl; when it is (1–4C)alkylsulphonyl is, for example, methylsulphonyl, ethylsulphonyl or propylsulphonyl; when it is N-(1–4C)alkylcarbamoyl is, for example N-methylcarbamoyl, N-ethylcarbamoyl and N-propylcarbamoyl; when it is N,N-di-[(1–4C)alkyl]-carbamoyl is, for example N,N-dimethylcarbamoyl, N-ethyl-N-methylcarbamoyl and N,N-diethylcarbamoyl; when it is (1–4C)alkylamino or (1–3C)alkylamino is, for example, methylamino, ethylamino or propylamino; when it is di-[(1–4C)alkyl]amino or di-[(1–3C)alkyl]amino is, for example, dimethylamino, N-ethyl-N-methylamino, diethylamino, N-methyl-N-propylamino or dipropylamino; when it is (2–4C)alkanoylamino is, for example, acetamido, propionamido or butyramido; when it is phenyl-(1–4C)alkyl is, for example benzyl or 2-phenylethyl; when it is phenyl-(1–4C)alkoxy is, for example benzyloxy; when it is —NHCO(1–4C)alkyl is, for example acetamido; when it is N-phthalimido-(1–4C)alkyl is, for example 2-(N-phthalimido)ethyl or 3-(N-phthalimido)propyl.

A suitable pharmaceutically-acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine, tris-(2-hydroxyethyl)amine, N-methylpiperidine, N-ethylpiperidine, procaine, dibenzylamine, N,N-dibenzylethylamine, N-methyl deglucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

In another embodiment there is provided a compound of formula (I) wherein $R^1$ is selected from (1–6C)alkyl [optionally substituted by one or two substituents independently selected from halo, amino, (1–4C)alkylamino, di-[(1–4C)alkyl] amino, hydroxy, cyano, (1–4C)alkoxy, (1–4C) alkoxycarbonyl, carbamoyl, —NHCO(1–4C)alkyl, trifluoromethyl, phenylthio, phenoxy], benzyl, (3–5C) alkenyl [optionally substituted by up to three halo substituents, or by one trifluoromethyl substituent, or one phenyl substituent], N-phthalimido-(1–4C)alkyl, (3–5C)alkynyl and (3–6C)cycloalkyl-(1–6C)alkyl;

wherein any phenyl or benzyl group in $R^1$ is optionally substituted by up to three substituents independently selected from halogeno, hydroxy, nitro, amino, (1–3C) alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C) alkyl]amino, hydroxy and trifluoromethyl], (3–5C) alkenyl [optionally substituted by up to three halo substituents, or by one trifluoromethyl substituent], (3–5C)alkynyl, (1–3 C)alkoxy, —SH, —S-(1–3 C)alkyl, carboxy, (1–3C)alkoxycarbonyl;

$Q_1$ and $Q_2$ are both phenyl;

and one or both of $Q_1$ and $Q_2$ bears on any available carbon atom one substituent of the formula (Ia) and $Q_2$ may bear on any available carbon atom further substituents of the formula (Ia) [provided that when present in $Q_1$ the substituent of formula (Ia) is not adjacent to the —NH— link];

wherein X is $CH_2$, O, NH or S; Y is H or as defined for Z; Z is OH, SH, $NH_2$, (1–4C)alkoxy, (1–4C)alkylthio, —NH(1–4C)alkyl, [N[(1–4C)alkyl]$_2$, pyrrolidin-1-yl, piperidin-1-yl, piperazin-1-yl, morpholino or thiomorpholino; n is 1, 2 or 3; n is 1, 2 or 3;

and $Q_1$ and $Q_2$ may each optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–3C)alkyl, fluoro-(1–4C)alkyl, amino-(1–3C)alkyl, (1–4C) alkylamino-(1–3 C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-d[(1–4C)alkyl]-carbamoyl-(1–4C)alkyl, pyrrolidin-1-yl-(1–3 C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C) alkoxy, cyano-(1–4C)alkoxy, carbamoyl-(1–4C)

alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, ureido (H₂N—CO—NH—), (1–4C)alkylNH—CO—NH—, di-[(1–4C)alkyl]-N—CO—NH—, (1–4C)alkylNH—CO—N[(1–4C)alkyl]-, di-((1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or in addition to the above substituents, Q₁ and/or Q₂ may optionally bear on any available carbon atom up to two further substituents independently selected from phenyl-(1–4C)alkyl, phenyl-(1–4C)alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C)alkoxy substituents may optionally bear one or two substituents independently selected from halogeno, (1–4C)alkyl and (1–4C)alkoxy; or a pharmaceutically-acceptable salt or in-vivo-hydrolysable ester thereof.

In a further embodiment there is provided a compound of formula (I) wherein $R^1$ is selected from (1–6C)alkyl [optionally substituted by one or two substituents independently selected from halo, amino, (1–4C)alkylamino, di-(1–4C)alkylamino, hydroxy, cyano, (1–4C)alkoxy, (1–4C)alkoxycarbonyl and carbamoyl], benzyl, (2–4C)alkenyl, (2–5C)alkynyl and (3–6C)cycloalkyl-(1–6C)alkyl;

$Q_1$ and $Q_2$ are both phenyl;

and one or both of $Q_1$ and $Q_2$ bears on any available carbon atom that is not adjacent to the —NH— or —NR¹— link one or more substituents of the formula (Ia)

wherein X is CH₂, O, NH or S; Y is H or as defined for Z; Z is OH, SH, NH₂, (1–4C)alkoxy, (1–4C)alkylthio, —NH(1–4C)alkyl, —N [(1–4C)alkyl]₂, pyrrolidin-1-yl, piperidin-1-yl, piperazin-1-yl, morpholino or thiomorpholino; n is 1, 2 or 3; m is 1, 2 or 3;

and $Q_1$ and $Q_2$ may each optionally bear on any available carbon atom up to four substituents independently selected from halogeno, hydroxy, oxo, thioxo, nitro, carboxy, cyano, (2–4C)alkenyl, (2–4C)alkynyl, (1–5C)alkanoyl, (1–4C)alkoxycarbonyl, (1–4C)alkyl, hydroxy-(1–3 C)alkyl, fluoro-(1–4C)alkyl, amino-(1–3 C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3 C)alkyl, piperidin-1-yl-(1–3 C)alkyl, piperazin-1-yl-(1–3C)alkyl, morpholino-(1–3 C)alkyl, thiomorpholino-(1–3C)alkyl, (1–4C)alkoxy, cyano-(1–4C)alkoxy, carbamoyl-(1–4C)alkoxy, N-(1–4C)alkytcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (2–4C)alkenyloxy, (2–4C)alkynyloxy, (1–4C)alkylthio, (1–4C)alkylsulphinyl, (1–4C)alkylsulphonyl, ureido, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, phenyl-(1–4C)alkyl, phenyl-(1–4C)alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C)alkoxy substituents may optionally bear one or two substituents independently selected from halogeno, (1–4C)alkyl and (1–4C)alkoxy; or a pharmaceutically-acceptable salt or in-vivo-hydrolysable ester thereof.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy-(1–6C)alkyl esters for example 1-cyclohexylcarbonyloxyethyl; 1,3-dioxolan-2-onylmethyl esters for example 5-methyl-1,3-dioxoan-ylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl include chloromethyl, aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification. Further suitable in-vivo hydrolysable esters of a compound of the formula (I) are described as follows. For example, a 1,2-diol may be cyclised to form a cyclic ester of formula (PD1) or a pyrophosphate of formula (PD2):

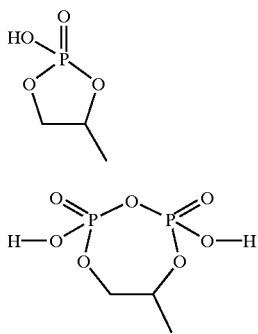

(PD1)

(PD2)

Esters of compounds of formula (I) wherein the HO— function/s in (PD1) and (PD2) are protected by (1–4C)alkyl, phenyl or benzyl are useful intermediates for the preparation of such pro-drugs.

Further in-vivo hydrolysable esters include phosphoramidic esters, and also compounds of formula (I) in which any free hydroxy group independently forms a phosphoryl (npd is 1) or phosphiryl (npd is 0) ester of the formula (PD3):

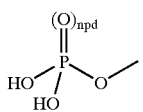

(PD3)

Useful intermediates for the preparation of such esters include compounds containing a group/s of formula (PD3) in which either or both of the —OH groups in (PD3) is independently protected by (1–4C)alkyl, phenyl or phenyl-(1–4C)alkyl (such phenyl groups being optionally substituted by 1 or 2 groups independently selected from (1–4C) alkyl, nitro, halo and (1–4C)alkoxy).

Thus, prodrugs containing groups such as (PD1), (PD2) and (PD3) may be prepared by reaction of a compound of formula (I) containing suitable hydroxy group/s with a suitably protected phosphorylating agent (for example, containing a chloro or dialkylamrino leaving group), followed by oxidation (if necessary) and deprotection.

When a compound of formula (I) contains a number of free hydroxy group, those groups not being converted into a prodrug functionality may be protected (for example, using a t-butyl-trimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

Some compounds of the formula (I) may have chiral centres and/or geometric isomeric centres (E- and Z-isomers), and it is to be understood that the invention encompasses all such optical, diastereo-isomers and geometric isomers, and mixtures thereof, that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

Particular preferred compounds of the invention comprise a pyrimidine derivative of the formula (I), or pharmaceutically-acceptable salt or in-vivo hydrolysable ester thereof, wherein $R^1$, $Q_1$, $Q_2$, X, Y, Z, m and n have any of the meanings defined hereinbefore, or any of the following values. Such values may be used where appropriate with any of the definitions, claims or embodiments defined hereinbefore or hereinafter.

(a0) When $Q_1$ or $Q_2$ is indanyl or 1,2,3,4-tetrahydronaphthyl, it is linked via the unsaturated ring; preferably $Q_1$ and/or $Q_2$ are (both) phenyl;

(a1) In another embodiment $R^1$ is preferably benzyl, (3–5C) alkynyl (especially propyn-2-yl), (3–6C)cycloalkyl-(1–6C)alkyl (especially cyclopropylmethyl), (1–4C)alkyl [optionally substituted by one or two substituents selected from hydroxyy, amino, halo, trifluoromethyl and cyano] or (3–5C)alkenyl substituted by one to three halo groups;

(b) $R^1$ is preferably benzyl, (3–5C)alkynyl (especially propyn-2-yl), (3–6C)cycloalkyl-(1–6C)alkyl (especially cyclopropylmethyl), (1–4C)alkyl [optionally substituted by one substituent selected from hydroxy, amino, halo, trifluoromethyl and cyano] or (3–5C)alkenyl substituted by one halo group;

(c) $R^1$ is more preferably (3–5C)alkynyl (especially propyn-2-yl) or (1–4C)alkyl [optionally substituted by trifluoromethyl or cyano] or (3–5C)alkenyl substituted by one bromo group;

(d) $R^1$ is most preferably propyn-2-yl, (1–4C)alkyl substituted by one trifluoromethyl or one cyano group (especially cyanomethyl or 2-cyanoethyl) or (3–5C) alkenyl substituted by one bromo group (especially —CH$_2$CH=CHBr);

(e) $R^1$ is most especially preferred as —CH$_2$CH=CHBr, —CH$_2$CH$_2$CH$_2$CF$_3$ or —CH$_2$CH=CH-phenyl;

(e1) In another embodiment $R^1$ is preferred as propyn-2-yl, cyanomethyl, 2-cyanoethyl, —CH$_2$CH=CHBr or —CH$_2$CH$_2$CH$_2$CF$_3$ (especially —CH$_2$CH$_2$CH$_2$CF$_3$);

(f) In one embodiment Z is preferably —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino; or alternatively Z is NH$_2$;

(f1) In one embodiment Y is preferably H, OH, SH, NH$_2$, (1–4C)alkoxy, (1–4C)alkylthio, —NH(1–4C)alkyl, —N[(1–4C)alkyl]$_2$or —NH-(3–8C)cycloalkyl; especially H or OH;

(f2) In one embodiment X is preferably O or NH or NRx; least preferred is X as S;

(f3) Preferably n+m is less than 5;

(f3) Preferably in the substituent of formula (Ia) X is O, Y is H or OH and Z is —NH(1–4C)alkyl, —N[(1–4C)alkyl]$_2$ or —NH-(3–8C)cycloalkyl; preferably n is 1 and m is 1;

(f4) In another embodiment in the substituent of formula (Ia) X is O, Y is OH and Z is —N[(1–4C)alkyl]$_2$; preferably n is 1 and m is 1;

(g) Most preferably the substituent of formula (Ia) is 3-dimethylamino-2-hydroxypropoxy;

(h) Preferably there is one substituent of formula (Ia), and this substituent is in ring Q$_1$ (i.e a ring linked via —NH—);

(i) When the substituent of formula (Ia) is in Q$_1$ it must be in either the para- or meta-position relative to the —NH—, preferably in the para-position;

(j) Preferably Q$_1$ bears no further substituents (other than (Ia)); preferable further substituents for Q$_2$include halo, hydroxy-(1–3C)alkyl, fluoro-(1–4C)alkyl (especially trifluoromethyl), morpholino and (1–4C)alkyl (especially methyl);

(k) More preferable further substituents for Q$_2$ include halo, morpholino and (1–4C)alkyl (especially methyl);

(l) Preferably the ring Q$_1$ or Q$_2$ not bearing the substituent of formula (Ia) is substituted by one or two further substituents, preferably halo, morpholino and/or (1–4C) alkyl (especially methyl);

(m) Most preferably the ring Q$_1$ bears the substituent of formula (Ia) and Q$_2$ is substituted by one or two further substituents, selected preferably from halo, hydroxy-(1–3 C)alkyl, fluoro-(1–4C)alkyl (especially trifluoromethyl), morpholino and (1–4C)alkyl (especially methyl).

A preferred compound of the invention is a pyrimidine derivative of the formula (I), or pharmaceutically-acceptable salt or in-vivo hydrolysable ester thereof as claimed in any of claims 1 to 5 and wherein (i) Q$_2$ does not bear any optional further substituents of formula (Ia) and/or (ii) there is one substituent of formula (Ia), borne by Q$_1$ and/or (iii) in claims 1 or 2 Q$_1$ does not bear any of the additional two further substituents that are listed.

A further preferred compound of the invention is a pyrimidine derivative of the formula (I), or pharmaceutically-acceptable salt or in-vivo hydrolysable ester thereof, wherein:

Q$_1$ and Q$_2$ are both phenyl;

R$^1$ is (1–4C)alkyl substituted by one cyano group (especially cyanomethyl);

or alternatively R$^1$ is —CH$_2$CH═CHBr or —CH$_2$CH$_2$CH$_2$CF$_3$ (especially —CH$_2$CH$_2$CH$_2$CF$_3$) or —CH$_2$CH═CH-phenyl;

Q$_1$ bears one substituent of formula (Ia) (especially 3-dimethylamino-2-hydroxypropoxy), preferably in the para-position;

Q$_2$ bears one or two substituents independently selected from halo, morpholino and (1–4C)alkyl (especially methyl).

A specific preferred compound of the invention is the following pyrimidine derivative of the formula (I):

4-{4-[3-(N,N-Dimethyl)amino-2-hydroxy-propoxy] anilino}-6-(N-cyanomethyl-2-bromo-4-methylanilino) pyrimidine;

4-{4-[3-(N,N-Dimethyl)amino-2-hydroxy-propoxy] anilin}-6-(N-cyanomethyl-2-chloro-5-methylanilino) pyrimidine;

4-{4-[3-(N,N-Dimethyl)amino-2-hydroxy-propoxy] anilino}-6-(N-(3-phenylprop-2-enyl)-2-bromo-4-methylanilino)pyrimidine; or pharmaceutically-acceptable salt or in-vivo hydrolysable ester thereof.

Other specific preferred compounds of the invention are the pyrimidine derivatives of the formula (I), described in Examples 6, 10, 19 and 20, or pharmaceutically-acceptable salts or in-vivo hydrolysable esters thereof.

Process Section

A pyrimidine derivative of the formula (I), or a pharmaceutically-acceptable salt or an in vivo hydrolysable ester thereof, may be prepared by any process known to be applicable to the preparation of chemically-related compounds. Such processes, when used to prepare a pyrimidine derivative of the formula (I), or a pharmaceutically-acceptable salt or an in vivo hydrolysable ester thereof, are provided as a further feature of the invention and are illustrated by the following representative examples in which, unless otherwise stated R$^1$, Q$_1$, Q$_2$, X, Y, Z, m and n have any of the meanings defined hereinbefore for a pyrimidine derivative of the formula (I) and unless another substituent is drawn on ring Q$_1$ or Q$_2$ the ring may bear any of the substituents described hereinbefore (optionally protected as necessary). Where a substituent is drawn on ring Q$_1$, this includes (unless stated otherwise) the possibilities of the substituent/s being on ring Q$_2$ in addition to, or instead of the substituent being on ring Q$_1$. Where X is defined in this process section as NH it is to be understood that this also includes the possibility of X as NRx.

Necessary starting materials may be obtained by standard procedures of organic chemistry (see, for example Advanced Organic Chemistry (Wiley-interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

Thus, as a further feature of the invention there are provided the following processes which comprises of:

a) reacting a pyrimidine of formula (II):

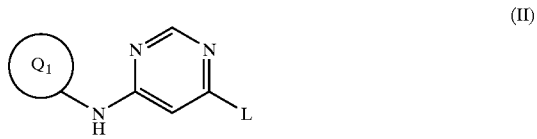

(II)

wherein L is a displaceable group as defined below, with a compound of formula (III):

(III)

b) reaction of a pyrimidine of formula (IV):

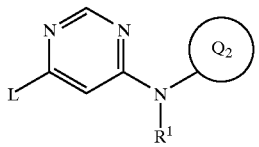
(IV)

wherein L is a displaceable group as defined below, with a compound of formula (V):

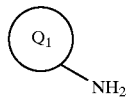
(V)

c) reacting a pyrimidine of formula (VI):

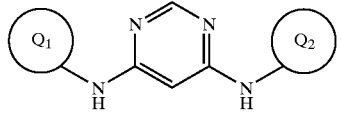
(VI)

with a compound of formula (VII)

R¹—L   (VII)

wherein L is a displaceable group as defined below;

d) for compounds of formula (I) where n=1, 2 or 3; m=1 and Y is OH, NH, or SH, reaction of a 3-membered heteroalkyl ring of formula (VIII):

(VIII)

wherein A is O, S or NH;
with a nucleophile of formula (IX):

Z—D   (IX)

wherein D is H or a suitable counter-ion;

e) for compounds of formula (I) where X is oxygen, by reaction of an alcohol of formula (X):

(X)

with an alcohol of formula (XI):

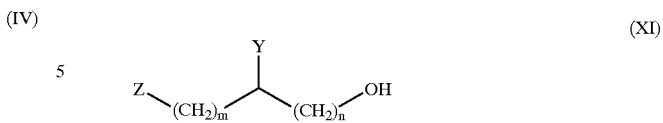
(XI)

f) for compounds of formula (I) wherein X is CH₂, O, NH or S; Y is OH and In is 2 or 3;
reaction of a compound of formula (XII):

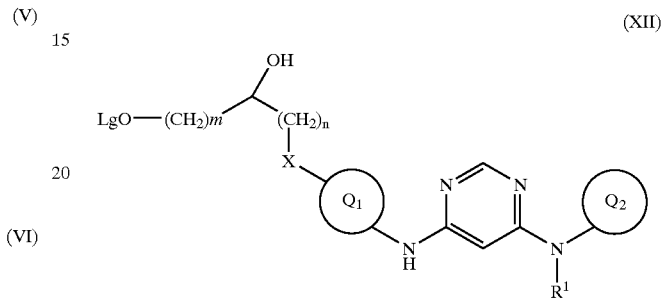
(XII)

wherein —OLg is a leaving group such as mesylate or tosylate; with a nucleophile of formula Z—D (IX) wherein D is H or a suitable counter-ion;

g) for compounds of formula (I) wherein X is CH₂, O, NH or S; Y is H; n is 1, 2 or 3 and m is 1, 2 or 3:
reaction of a compound of formula (XIII):

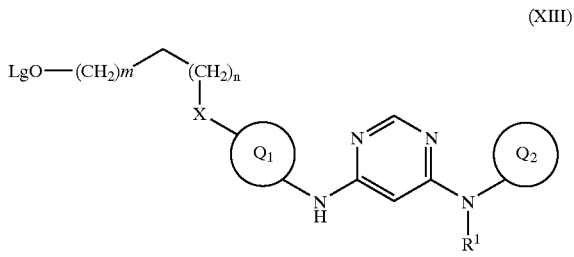
(XIII)

wherein —OLg is a leaving group such as mesylate or tosylate; with a nucleophile of formula Z—D (IX) wherein D is H or a suitable counter-ion;

h) for compounds of formula (I) wherein X is O, NH or S; Y is H; n is 1, 2 or 3 and m is 1, 2 or 3; reaction of a compound of formula (XIV) with a compound of formula (XV):

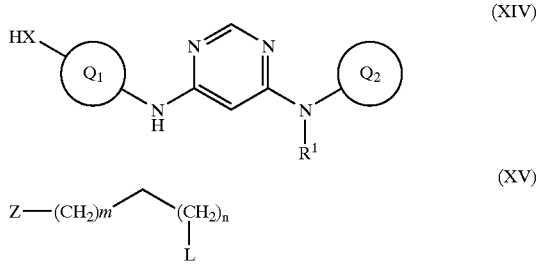
(XIV)

(XV)

or i) for compounds of formula (I) in which Z is SH, by conversion of a thioacetate group in a corresponding compound; and thereafter if necessary:
   (i) converting a compound of the formula (I) into another compound of the formula (I);
   (ii) removing any protecting groups;
   (iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

D is hydrogen or a counter-ion. When D is a counter-ion, suitable values for D include sodium and potassium.

Specific reaction conditions for the above reactions are as follows:

Process a)

Pyrimidines of formula (II) and compounds of formula (III) may be reacted together
   i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2-dimethoxyethane, N,N-dimethylformamide, N,N-dimethylacetamide or N-methylpyrrolidin-2-one, and at a temperature in the range, for example, 0° to 150° C., conveniently at or near reflux temperature; or
   ii) under standard Buchwald conditions (for example see J. Am. Chem. Soc., 118, 7215; J. Am. Chem. Soc., 119, 8451; J. Org. Chem., 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

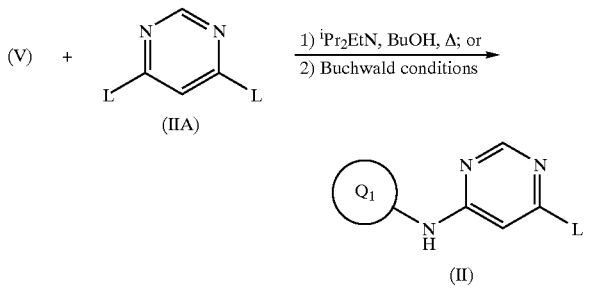

Compounds of formula (III) are commercially available or are prepared by processes known in the art.

Process b)

Pyrimidines of formula (IV) and compounds of formula (V) may be reacted together
   i) in the presence of a suitable solvent for example a ketone such as acetone or an alcohol such as ethanol or butanol or an aromatic hydrocarbon such as toluene or N-methyl pyrrolidine, or a solvent such as tetramethylene sulphone, optionally in the presence of a suitable acid such as those defined above and at a temperature in the range of 0° C. to reflux, preferably reflux; or
   ii) under standard Buchwald conditions as described above, Pyrimidines of formula (IV) are prepared according to the following scheme:

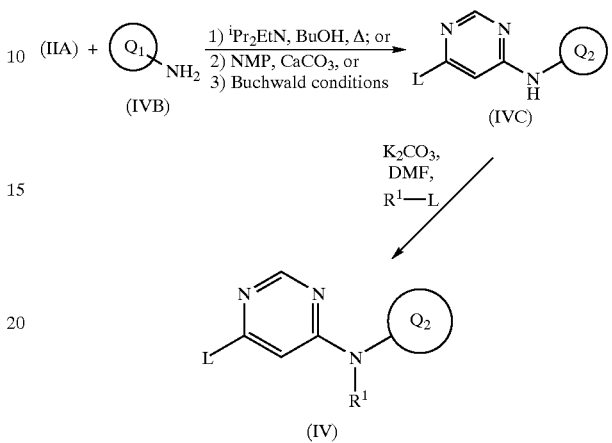

wherein L is a displaceable group as defined above.

The compounds of formula (V) are commercially available or are prepared by processes known in the art.

Process c)

Pyrimidines of formula (VI) and compounds of formula (VII) are reacted together in the presence of a suitable base such as sodium hydride or potassium carbonate or potassium tert-butoxide and a suitable solvent such as N,N-dimethylformamide, dimethyl sulfoxide or tetrahydrofuran at a temperature in the range of −20° to 110° C., preferably −20° to 60° C.

Compounds of formula (VI) may be prepared according to the following scheme:

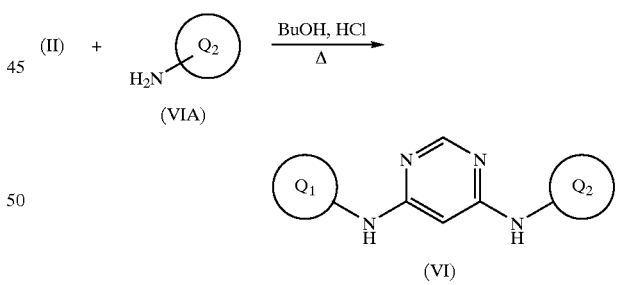

Process d)

Three membered heteroalkyl rings of formula (VIII) and nucleophiles of formula (IX) are reacted together at a temperature in the range of 20° to 100° C., preferably 20° to 50° C., optionally in the presence of a suitable solvent, for example N,N-dimethylformamide, dimethyl sulfoxide or tetrahydrofuran.

Compounds formula (VIII) may be prepared according to the following schemes:

Scheme I) for compounds of formula (VIII) where A is O, and X is not carbon:

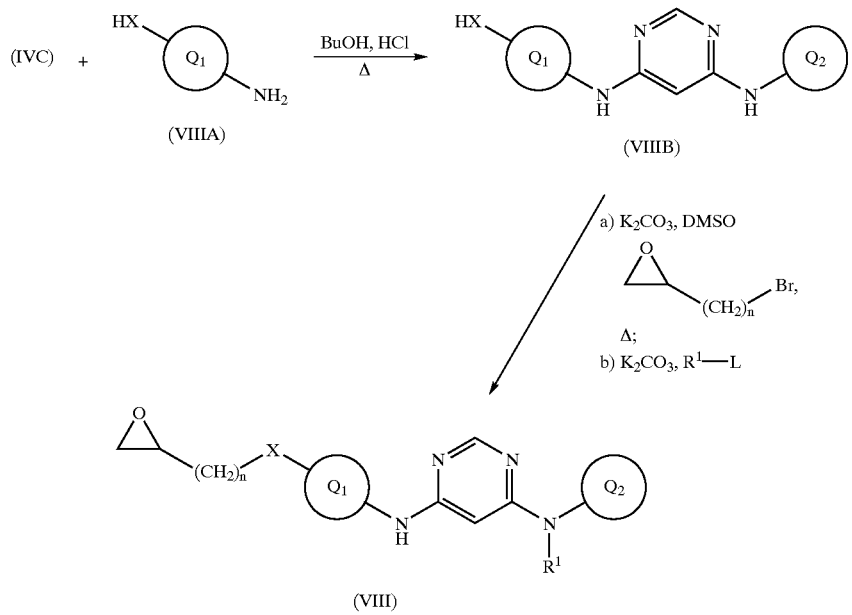

The conversion of (VIIIB) to (VIII) may also be achieved by reaction with Br—(CH$_2$)$_n$—CHO, or an equivalent ester, in DMF and the presence of a base, followed by reaction with a sulfur ylide such as (Me$_2$SOCH$_2$) in an inert solvent such as THF (see Scheme V); followed by reaction with R$^1$—L.

Scheme II) for compounds of formula (VIII) where A is NH, and X is not carbon:

Scheme III) for compounds of formula (VIII) where A is S, and X is not carbon:

(VIIIC) $\xrightarrow{\text{1) (EtO)}_2\text{P(S)SBr, DCM.} \quad \text{2) TBAF.}}$

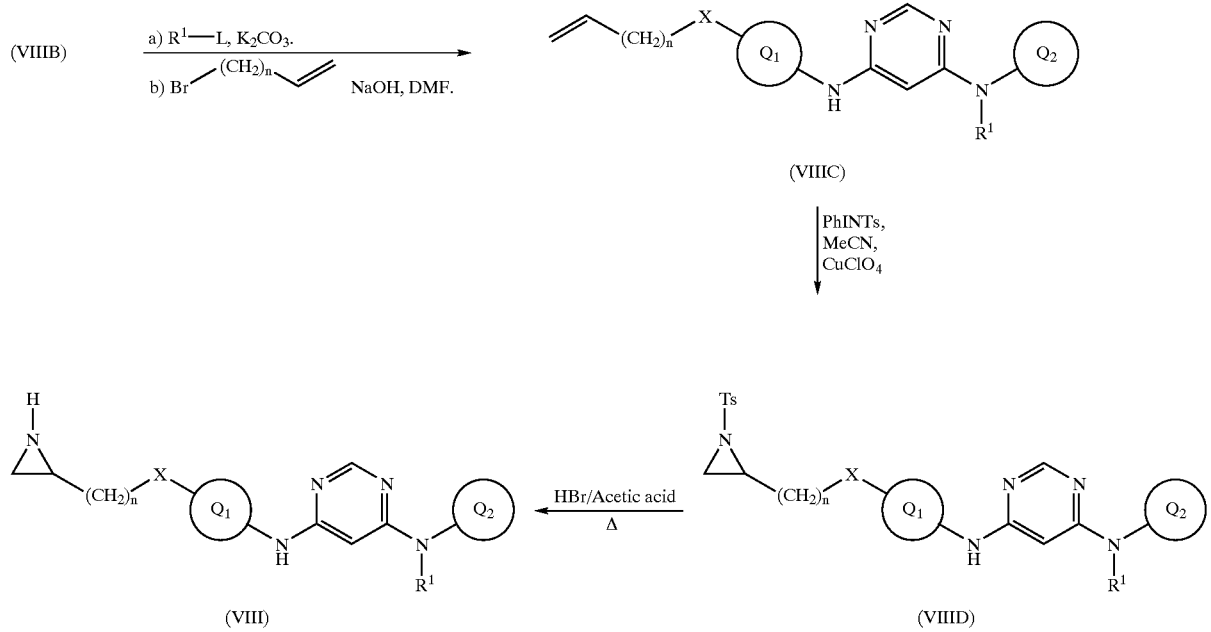

(for PhINTs see, for example. Tet.Let., 1997, 38 (39), 6897–6900; compounds of formula (VIIIC) may also be oxidised to the epoxide using conditions similar to that in Scheme IV) below);

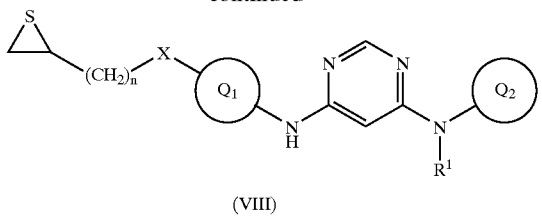

(VIII)

(for example see *Synlett*. 1994, 267–268);
Scheme IV) For compounds of formula (VIII) where X is carbon

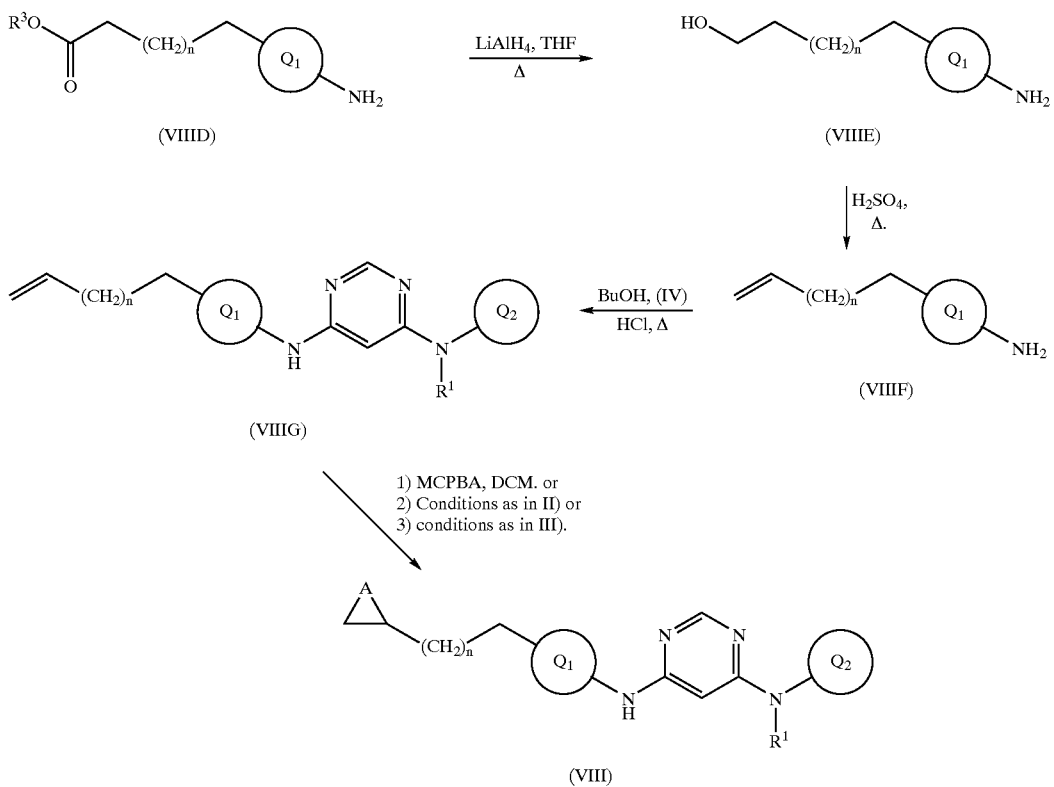

(XB) is reacted with (IVC) (see Scheme I) and then $R^1$—L to give (VIII).

An equivalent ester of (XA) may also be used. See also Russ.Chem. Rev. 47, 975–990, 1978.

Compounds of formula (VII), (IX), (VIIIA) and (VIIID) are commercially available or are prepared by processes known in the art.

Process e)

Alcohols of formula (X) and (XI) can be reacted together under standard Mitsunobu conditions. For example in the presence of diethyl azodicarboxylate and triphenyl phosphine, in a suitable solvent such as dichloromethane, toluene or tetrahydrofuran, and at a temperature in the range of 0° to 80° C., preferably in the range of 20° to 60° C.

wherein $R^3$ together with the —COO— group to which it is attached forms an ester moiety, for example a methyl ester or an ethyl ester.

Scheme V) For compounds of formula (VIII) wherein X is $CH_2$, O, NH or S; Y is OH; n is 1, 2 or 3 and m is 1:

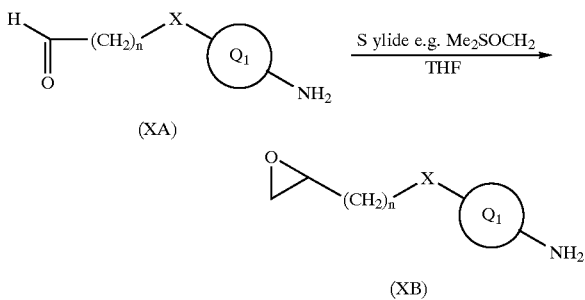

Alcohols of formula (X) are made according to the process in Scheme I) above for the synthesis of intermediate (VIIIB) (where X is oxygen).

Alcohols of formula (XI) are commercially available or are made by processes known in the art.

In a process analogous to process e), compounds in which X is S may be prepared by reaction of a compound of formula (X) in which the hydroxy group is —SH, with a compound of formula (XI) in which the hyrdoxy group is a leaving group such as mesylate or tosylate.

Process f)

Compounds of formula (XII) wherein X is $CH_2$, O, NH or S; Y is OH and m is 2 or 3 and nucleophiles of formula (IX) are reacted together at a temperature in the range of 20° to 100° C., preferably 20° to 50° C., optionally in the presence of a suitable solvent, for example N,N-dimethylformamide, dimethyl sulphoxide or tetrahydrofuran,and optionally in the presence of a suitable base, such as potassium carbonate.

Compounds of formula (XII) are prepared according to the following scheme (m is 2 or 3):

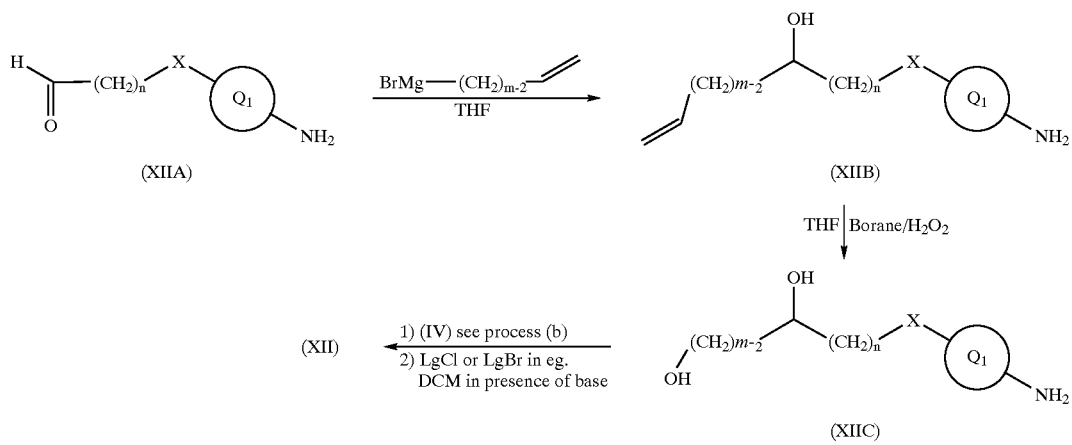

The steps 1) and 2) in the final step may be reversed. A suitable base for step 2) is triethylamine.

Compounds of formula (XIIA) and (IX) are commercially available or are prepared by processes known in the art. For example, compounds of formula (XIIA) in which X is NH, O or S may be prepared by reaction of a compound of formula (VIIIA) with a suitable haloaldehyde or equivalent ester under standard conditions for such reactions.

Process g)

Compounds of formula (XIII) and nucleophiles of formula (IX) are reacted together as described for process f) above.

Compounds of formula (XIII) are prepared in an analogous manner to step 2) in the final step of the process for preparing compounds of formula (XII) above. The necessary primary alcohol starting materials are commercially available or are prepared by processes known in the art.

Process h)

Compounds of formula (XIV) and (XV) are reacted in an inert solvent such as DMF in the presence of a base such as potassium carbonate.

Compounds of formula (XIV) are prepared as described in Scheme I), but omitting the first stage of the final step (i.e. no reaction with the epoxide). Compounds of formula (XV) are commercially available or are prepared by processes known in the art.

Process i)

For the compounds of formula (I) in which Z is SH, the conversion of a thioacetate group in a corresponding compound is carried out as described herein for the conversion of compounds of formula (IJ) into (IK).

Suitable starting materials containing a thioacetate group are prepared from corresponding compounds containing a leaving group such as mesylate or tosylate (prepared using standard conditions from the corresponding hydroxy compound) using thiol acetic acid as described herein for the conversion of compounds of formula (IG) into (IJ).

Examples of conversions of a compound of formula (I) into another compound of formula (I) are:

Conversion i) conversion of $R^1$ as a substituted side chain into another substituted side chain, for example:

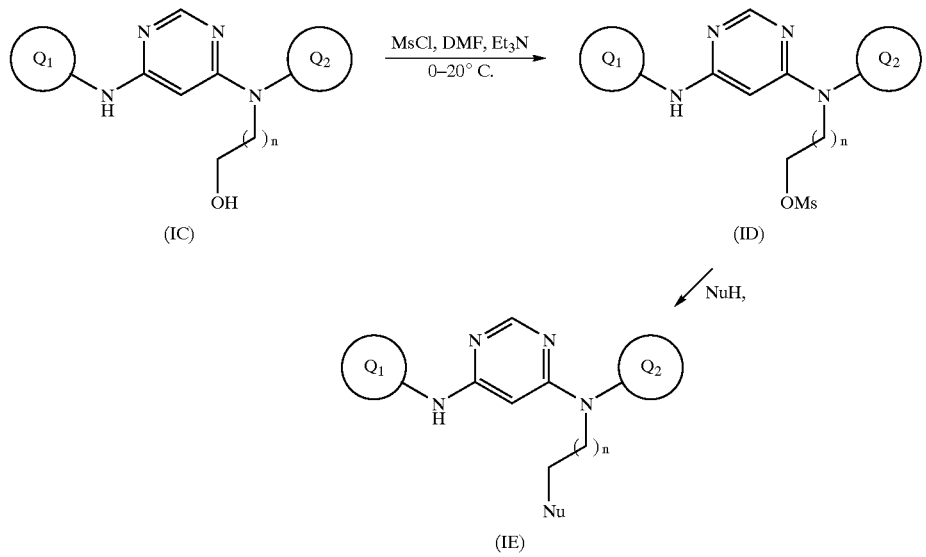

wherein Ms is methanesulphonyl, and Nu is a nucleophile that introduces a substituent that is an optional substituent for $R^1$ as defined in formula (I), preferably Nu is $-NH_2$, $-NHC_{1-4}alkyl$, $-N(C_{1-4}alkyl)_2$ or $-CN$ (NB the hydroxyl moiety does not necessarily have to be on the terminal carbon as depicted above);

Conversion ii): conversion of one side chain of formula (Ia) into another side chain of formula (Ia), for example:

EXAMPLE I for compounds of formula (I) where Y is $NH_2$ (depicted below using ammonia), (1–4C)alkoxy, (1–4C)alkylthio, $-NH(1-4C)alkyl$, $-N[(1-4C)alkyl]_2$, pyrrolidin-1-yl, piperidin-1-yl, piperazin-1-yl, morpholino or thiomorpholino;

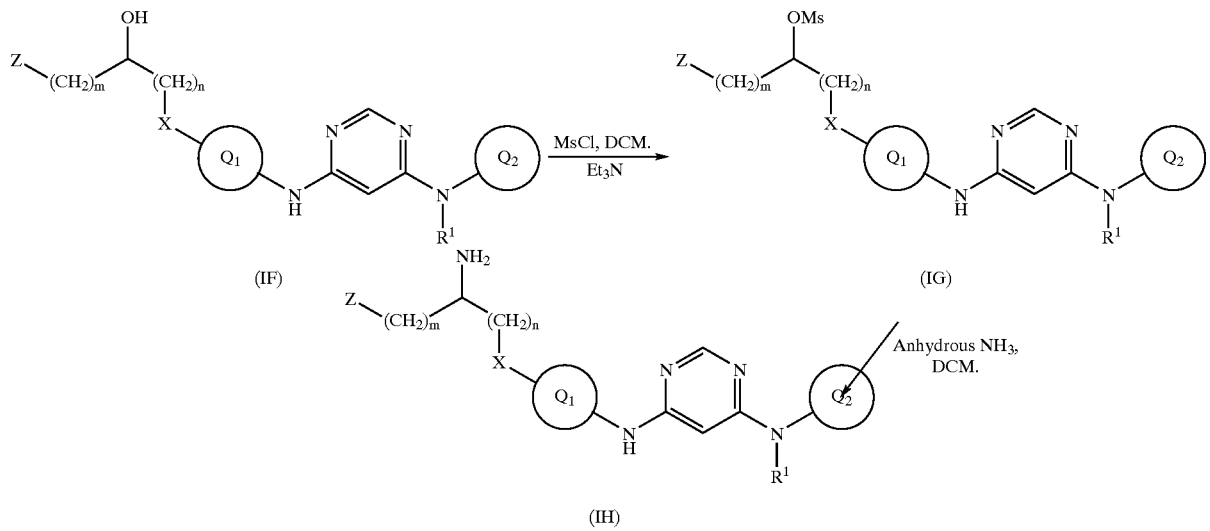

or:

EXAMPLE II
for compounds of formula (1) where Y is S:

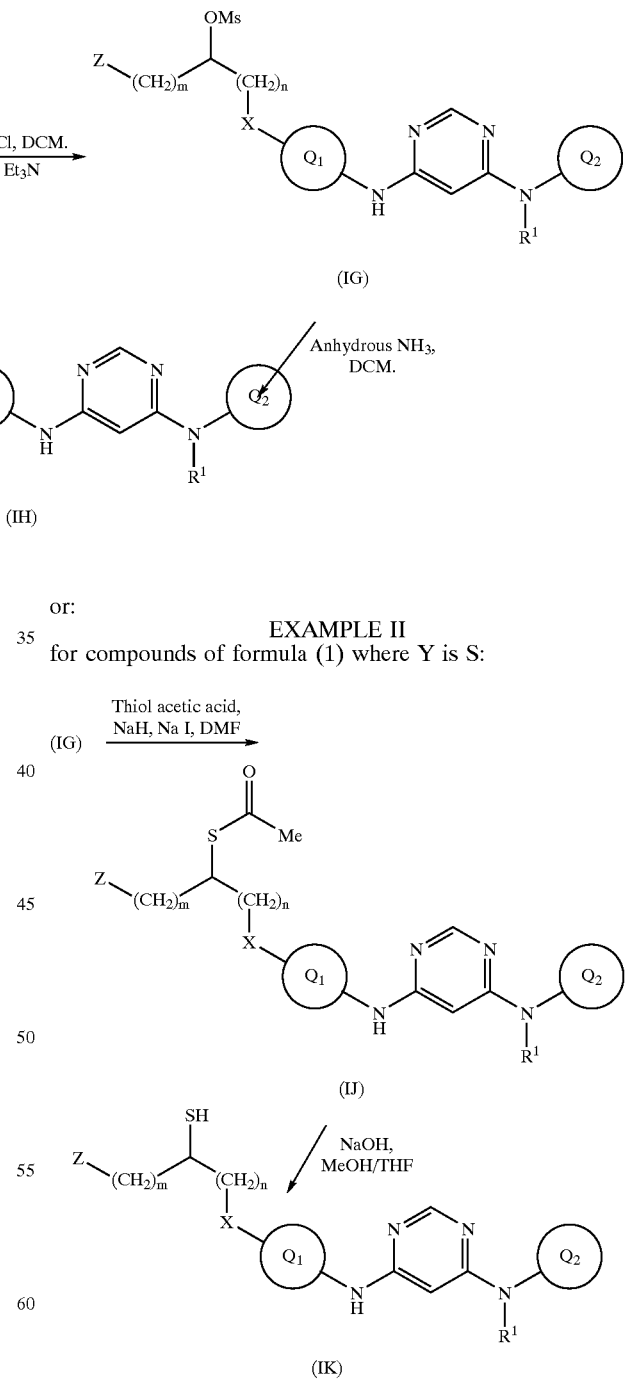

EXAMPLE III
for compounds of formula (I) where Y is H:

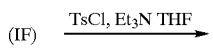

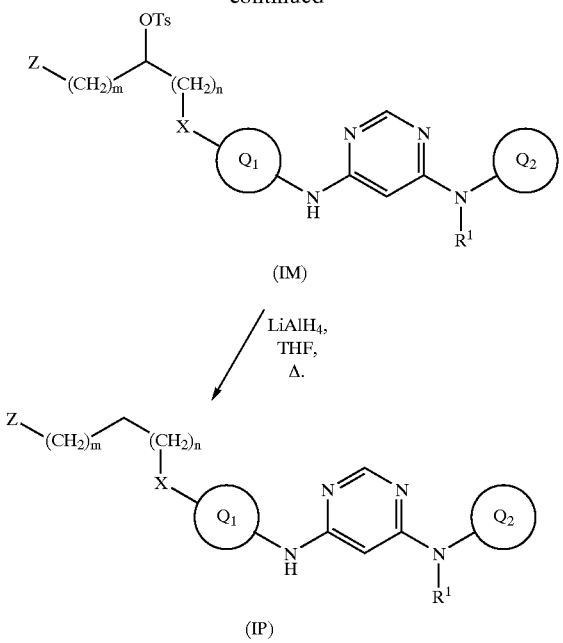

(IM)

(IP)

The skilled reader will appreciate that the manipulation of the side chain (Ia) described in Processes c), d), e), f), g) and h) and Conversion ii) above and of the sidechain $R^1$ in Conversion i) above may also be performed on intermediates for example to make intermediates of formula (II), (IIA), (IIB), or (V). For example:

alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example

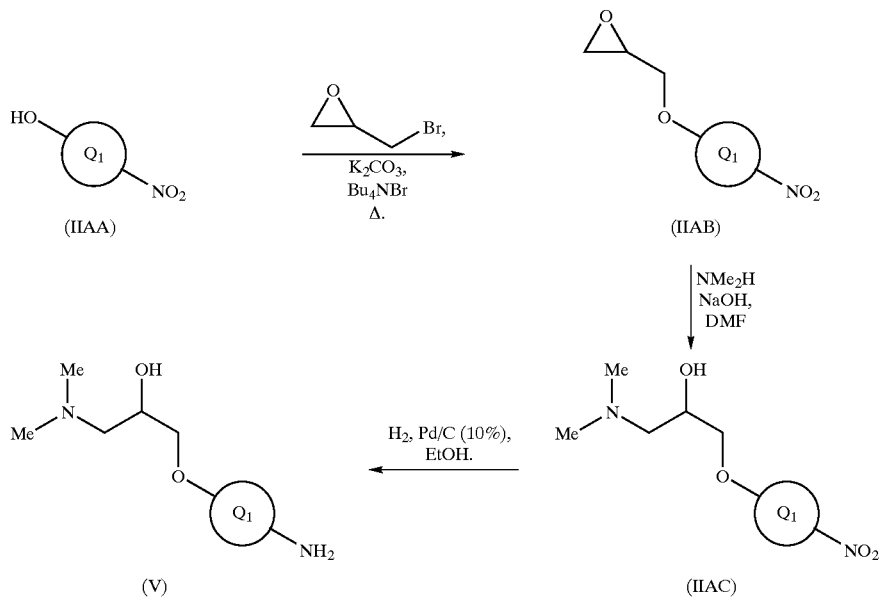

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, benzoyl. The deprotection conditions for the above protecting groups necessarily vary with the choice of protecting group. Thus, for example an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl Croup may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula (II) and (IV) and these are provided as a further feature of the invention.

Assays

As stated hereinbefore the pyrimidine derivative defined in the present invention possesses anti-cell-proliferation activity such as anti-cancer activity which is believed to arise from the CDK inhibitory activity of the compound. These properties may be assessed, for example, using the procedure set out below:

CDK Inhibition Assay

The following abbreviations have been used:

HEPES is N-[2-Hydroxyethyl]piperazine-N'-[2-ethanesulfonic acid]

DTT is Dithiothretiol

PMSF is Phenylmethylsulfonyl fluoride

The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma). In each well was placed the compound to be tested (diluted in DMSO and water to correct, concentrations) and in control wells either p 16 as an inhibitor control or DMSO as a positive control.

Approximately 0.5 µl of CDK4/Cyclin D1 partially-purified enzyme (amount dependent on enzyme activity) diluted in 25 µl incubation buffer was added to each well then 20 µl of GST-Rb/ATP/ATP33 mixture (containing 0.54 µg GST-Rb and 0.2 µM ATP and 0.14 µCi [γ-33-P]-Adenosine Triphosphate), and the resulting mixture shaken gently, then incubated at room temperature for 60 minutes.

To each well was then added 150 µL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM MnCl$_2$, 1 mM DTT, 100 µM Sodium vanadate, 100 µM NaF, 10 mM Sodium Glycerophosphate, BSA (1 mg/ml final).

As a control, another known inhibitor of CDK4 may be used in place of p16.

Test Substrate

In this assay only part of the retinoblastoma (Science 1987 Mar13;235(4794):1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression internal lac I$^q$ gene for use in any E.Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E.Coli (BL21 (DE3) pLysS cells ) using standard inducible expression techniques, and purified as follows.

E.coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech. Herts. UK), and washed with NETN buffer. After washing with kinase buffer (50 mMN HEPES pH 7.5. 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from NICF-7 cell line (obtained from ATCC number:HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell 1992 Oct 16; 71(2): 323–334; Matsushime H., Ewen M. E., Stron D. K., Kato J. Y., Hanks S. K., Roussel M. F., Sherr C. J. and Cyclin D1 amino acids 1–296; Ref. Cold Spring Harb. Symp. Quant. Biol., 1991; 56:93–97; Amold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V1392-20). The PCR products were then dually expressed [using a standard virus Baculogold co-infection technique] into the insect SF21 cell system (Spodoptera Frugiperda cells derived from ovarian tissue of the Fall Army Worm—commercially available).

The following Example provides details of the production of Cyclin D1/CDK4 in SF21 cells (in TC100+10% FBS (TCS)+0.2% Pluronic) having dual infection MOI 3 for each virus of Cyclin D1 & CDK4.

Example Production of Cyclin D1/CDK4

SF21 cells crown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

$$Cyclin\ D1\ \frac{1.86 \times 10E6 \times 500 \times 3}{0.9 \times 10^8} =$$

31 ml of virus of each 500 ml. bottle.

$$CDK4\ \frac{1.86 \times 10E6 \times 500 \times 3}{1 \times 10^8} = 28\ \text{ml of virus for each 500 ml. bottle.}$$

The viruses were mixed together before addition to the cultures, and the cultures returned to the roller rig 28° C.

After 3 days (72 hrs.) post infection the 5 Litres of culture was harvested. The total cell count at harvest was 1.58×10E6 cells/ml.(99% viable). The cells were spun out at 2500 rpm, 30 mins., 4° C. in Heraeus Omnifuge 2.0 RS in 250 mls. lots. The supernatant was discarded.

20 pellets of ~4×10E8 cells/pellet were snap frozen in $LN_2$ and stored at −80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, 0.1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.4/100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US). p16 Control (Nature 366.:704–707; 1993: Serrano M. Hannon G J. Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref. Studier F. W. and Mtoffat B. A., J. Mol. Biol., 189, 113, 1986). A 1 liter culture was grown to the appropriate OD then induced with IPTG to express p16 overnight. The cells were then lysed by sonication in 50 mM sodium phoshate, 0.5 M sodium chloride, PMSF, 0.5 µg/mL leupeptin and 0.5 µg/mL aprotinin. The mixture was spun doen, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

pTB375

The background vector used for generation of pTB 375 was pZEN0042 (see UK patent 2253852) and contained the tetA/tetR inducble tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzvmes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cvclin E (see EMBL Accession No. M73812), and further details for such assays are contained in PCT International Publication No. WO99/21845, the relevant Biochemical & Biological Evaluation sections of which are hereby incorporated by reference.

If using CDK-2 with Cyclin E partial co-purification may be achieved as follows:

Sf21 cells are resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant is loaded onto a Poros HQ/M 1.4/100 anion exchange column (PE Biosystems, Hertford, UK). CDK-2 and Cyclin E are coeluted at the beginning of a 0–1M NaCl gradient (run in lysis buffer minus protease inhibitors) over 20 column volumes. Co-elution is checked by western blot using both anti-CDK-2 and anti-Cyclin E antibodies (Santa Cruz Biotechnology, California, US).

Although the pharmacological properties of the compounds of the formula (I) vary with structural change, in general activity possessed by compounds of the formula (I) in the above assays may be demonstrated at $IC_{50}$ concentrations or doses in the range 250 µM to 1 nM.

When tested in the above in-vitro assay the CDK4 inhibitory activity of Example 1 was measured as $IC_{50}$=0.11 µM and that of Example 2 as $IC_{50}$=0.07 µM.

The in-vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R.(1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 μl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DNISO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 μl SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically-acceptable salt or in-vivo hydrolysable ester thereof, as defined hereinbefore in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a mother aspect of the present invention there is provided a pyrimidine derivative of the formula (I), or a pharmaceutically-acceptable salt or in-vivo hydrolysable ester thereof, as defined hereinbefore for use in a method of treatment of the human or animal body by therapy.

We have found that the pyrimidine derivatives defined in the present invention, or a pharmaceutically-acceptable salt or in-vivo hydrolysable ester thereof, are effective cell cycle inhibitors (anti-cell proliferation agents), which property (without being bound by theory) is believed to arise from their (G1-S phase) CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a pyrimidine derivative of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically-acceptable salt or in-vivo hydrolysable ester thereof, are expected to inhibit the growth of those primary and recurrent solid tumours which are associated with CDKs, especially those tumours which are significantly dependent on CDK for their growth and spread, including for example, certain tumours of the colon, breast, prostate lung, vulva and skin.

It is further expected that a pyrimidine derivative of the present invention will possess activity against other cell-proliferation diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I), or a pharmaceutically-acceptable salt or in-vivo hydrolysable ester thereof, as defined hereinbefore for use as a medicament; and the use of a pyrimidine derivative of the formula (I), or a pharmaceutically-acceptable salt or in-vivo hydrolysable ester thereof, as defined hereinbefore in the manufacture of a medicament for use in the production of an anti-cancer, cell cycle inhibitory (anti-cell-proliferation) effect in a warm-blooded animal such as man. Particularly, a cell cycle inhibitory effect is produced at the G1-S phase by inhibition of CDK2, CDK4 and/or CDK6, especially CDK4 and CDK6.

According to a further feature of this aspect of the invention there is provided a method for producing an anti-cancer, cell cycle inhibitory (anti-cell-proliferation) effect in a warm-blooded animal, such as man, in need of such treatment which comprises administering to said animal an effective amount of a pyrimidine derivative as defined immediately above. Particularly, an inhibitory effect is produced at the G1-S phase by inhibition of CDK2, CDK4 and/or CDK6, especially CDK4 and CDK6.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, lodoxyfene), progestogens (for example megestrol acetate), aromatase inhibitors (for example anastrozole, letrazole, vorazole, exemestane), antiprogestogens, antiandrogens (for example flutamide, nilutamide, bicalutarnide, cyproterone acetate), LHRH agonists and antagonists (for example aoserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) as defined hereinbefore and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) and their pharmaceutically acceptable salts are also useful as pharmacological tools in the development and standardisation of in vitro and in vivo rest svstems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

EXAMPLES

The invention will now be illustrated in the following non-limiting Examples, in which standard techniques known to the skilled chemist and techniques analogous to those described in these Examples may be used where appropriate, and in which, unless otherwise stated:

(i) evaporations were carried out by rotary evaporation in vacuo and work-up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC), for example using an Anachem Sympur MPLC, were performed on Merck Kieselgel silica (Art. 9385) or Merck Lichroprep RP-18 (Art. 9303) reversed-phase silica obtained from E. Merck, Darmstadt, Germany; where a Mega Bond Elut column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DNISO (unless otherwise stated); at ambient temperature unless marked 373K; on the delta scale (ppm downfield from tetramethylsilane); using a Varian Gemini 2000 spectrometer operating at a field strength of 300 MHz or a Bruker DPX400 spectrometer operating at a field strength of 400 MHz; and peak multilicities are shown as follows: s, singlet; d, doublet; t, triplet; m, multiplet; br, broad; mass spectrometry (MS) was performed by electrospray on a VG platform;, (vi) intermediates were not generally fully characterised and purity was assessed by thin layer chromatography (TLC), high performance liquid chromatography (HPLC), infra-red (IR), MS or NMR analysis;

(vii) it is to be understood that in this Examples section certain symbols, such as $R_1$ and $R_2$, have been used to describe certain Examples in Tables, and that the use of such symbols should be read in context with the Examples to which they refer;

(viii) certain geometric isomers (such as in Examples 11 & 17) may exist as E- and Z-isomers; it is to be understood that where one isomer, or no particular isomer, is shown this refers to a mixture of both isomers;

(ix) the following abbreviations may be used hereinbefore or hereinafter:

| | |
|---|---|
| DMF | N,N-dimethylformamide; |
| CDCl₃ | deuterated chloroform; |
| MeOH-δ4 | deuterated methanol; |
| EA | elemental analysis; |
| NMP | 1-methyl-2-pyrrolidinone; |
| DEAD | diethyl azodicarboxylate; |
| DTAD | ditertbutyl azodicarboxylate; |
| EtOH | ethanol; |
| DIPEA | diisopropylethylamine; |
| DCM | dichloromethane; |
| TFA | trifluoroacetic acid; |
| EtOAc | ethyl acetate; and |
| DMSO | dimethylsulphoxide. |

Example 1

4-{4-[3-(N,N-Dimethyl)amino-2-hydroxyproroxy]
anilino}-6-(N-cyanomethyl-2-bromo-4-
methylanilino)pyrimidine To a solution of 4-(4-hydroxyanilino)-6-(N-cyanomethyl-2-bromo-4-methylanilino)pyrimidine (Reference Example 1, 560 mg) in DMSO (2 ml) was added potassium carbonate (565 mg) and epibromohydrin (280 mg) and the reaction mixture was stirred at ambient temperature for 24 hours. Dimethylamine (2M in MeOH, 2.72 ml) was added and the reaction was stirred for a further 5 hours. The mixture was poured into water (50 ml) and extracted with EtOAc. The organic extract was dried (MgSO₄) and evaporated. The residue was purified by column chromatography eluting with DCM:MeOH: concentrated ammonia; 87:12:1 to give the title compound (503 mg, 72%) as a solid. NMR: 2.16 (6H, s), 2.20–2.38 (5H, m), 3.70–3.92 (3H, m), 4.56–4.70 (1H, brd), 4.73 (1H, d), 4.97–514 (1H, brd), 5.29 (1H, s), 6.80 (2H, d), 7.33–7.41 (4H, m), 7.70 (1H, s), 8.31 (1H, s), 8.94 (1H, s); m/z 511 (MH⁺).

Example 2

4-{4-[3-(N,N-Dimethyl)amino-2-hydroxylropoxy]
anilino}-6-(N-cyanomethyl-2-chloro-5-
methylanilino)pyrimidine To a solution of 4-(4-hydroxyanilino)-6-(2-chloro-5-methylanilino)pyrimidine (Reference Example 6, 1.03 g) in DMSO (6 ml) was added potassium carbonate (870 mg) and epibromohydrin (474 mg) and the reaction was stirred for 18 hours. Potassium carbonate (1.3 g) and bromoacetonitrile (754 mg) were added and the mixture was stirred for a futher 4 hours. Dimethylamine (2M solution in MeOH, 6ml) was added and the reaction was stirred for an additional 4 hours. The mixture was concentrated and the residue partitioned between EtOAc and saturated aqueous sodium chloride solution. The organic extract was separated, dried (MgSO₄) and evaporated. The residue was purified by column chromatography eluting with DCM:MeOH:concentrated ammonia; 90:9:1 to give the title compound (230 mg, 16%) as an oil. NMR: 2.04 (6H, s), 2.08–2.15 (5H, m), 3.61–3.80 (3H, m), 4.00 (1H, d), 5.20 (1H, s), 6.69 (2H, d), 7.15–7.28 (3H, m), 7.46 (1H, d), 8.19 (1H, s), 8.84 (1H, s); m/z 467 (MH⁺).

Preparation of Starting Materials for Examples 1
and 2

The starting materials for the Examples above are either commercially available or are readily prepared by standard methods from known materials. For example the following reactions are illustrations but not limitations of the preparation of some of the starting materials used in the above reactions.

Method A

Reference Example 1

4-(4-Hydroxyanilino)-6-(N-cyanomethyl-2-bromo-4-
methylanilino)pyrimidine

To a solution of 4-(4-tertbutyldimethylsilyloxyanilino)-6-(N-cyanomethyl-2-bromo-4-methylanilino)pyrimidine (Reference Example 2, 890 mg) in tetrahydrofuran (1 ml) was added N,N,N,N-tetraburylammonium fluoride (1M solution in tetrahydrofuran, 2 ml). The reaction mixture was stirred at ambient temperature for 30 minutes. The solvent was evaporated and the residue partitioned between EtOAc and water. The organic layer was separated and dried (MgSO₄), evaporated and purified by column chromatography eluting with DCM:MeOH:concentrated ammonia; 95:4:1 to give the title compound (510 mg, 73%) as a solid. M/z 410 (MH⁺).

Method B

Reference Example 2

4-(4-Tertbutyldimethylsilyloxyanilino)-6-(N-
cyanomethyl-2-bromo-4-methylanilino)pyrimidine To a solution of 4-(4-tertbutyldimethylsilyloxyanilino)-6-(2-bromo-4-methylanilino)pyrimidine (Reference Example 3, 396 mg) in tetrahydrofuiran (1 ml) under nitrogen atmosphere was added portion wise sodium hydride (60% dispersion in mineral oil, 58 mg). The solution was stirred for 30 minutes. Bromoacetonitrile (131 mg) was added and the reaction stirred for a further 1 hour. The solvent was evaporated and the residue purified by column chromatography eluting with DCM:MeOH:concentrated ammonia; 97.8:2:0.2 to give the title compound (158 mg, 37%) as a solid. M/z 524 (MH⁺).

Method C

Reference Example 3

4-(4-Tertbutyldimethylsilyoxyanilino)-6-(2-bromo-
4-methylanilino)pyrimidine

To a solution of 4-(4-hydroxyanilino)-6-(2-bromo-4-methylanilino)pyrimidine (Reference Example 4, 4 g) in chloroform (120 ml) was added imidazole (2.2 g) and tert-butylchlorodimethylsilane (2.4 g) and the reaction mixture was stirred for 12 hours. A saturated aqueous solution of sodium hydrogencarbonate (50 ml) was added and the mixture stirred for a further 30 minutes. The organic extract was dried (MgSO₄) and evaporated to dryness. The residue was purified by column chromatography eluting with DCM-:MeOH:concentrated ammonia; 98.8:1:0.2 to give the title compound (4.3 g, 83%) as a white solid. M/z 485 (MH⁺).

Method D

Reference Example 4

4-(4-Hydroxyanilino)-6-(2-bromo-4-methylanilino)
pyrimidine

To a solution of 4-(4-hydroxyanilino)-6-chloropyrimidine (Reference Example 5, 5 g) was added 2-bromo-4-methylaniline (7.5 ml) and the reaction mixture was heated at 195° C. for 24 hours. The residue was absorbed onto silica and purified by column chromatography eluting with DCM- :MeOH (19:1) to give the title compound (336 mg, 4%). NMR: 2.28 (3H, s), 5.72 (1H, s), 6.68 (2H, d), 7.17 (3H, m), 7.39 (1H, d), 7.48 (1H, s), 8.05 (1H, s), 8.38 (1H, s), 8.65 (1H, s), 9.08 (1H, s); m/z 371 (MH⁺).

Method E

Reference Example 5

4-(4-Hydroxyanilino)-6-chloropyrimidine

To a solution of 4,6-dichloropyrimidine (24.8 g), ethanol (250 ml) and triethylamine (51 ml) was added 4-aminophenol (18.2 g) and the solution was heated at reflux for 6 hours. After cooling the precipitate was collected, washed with DCM (100 ml) and recrystallized in acetonitrile to give the title compound (25.6 g, 69%) as crystals. NMR: 6.59 (1H, s), 6.73 (2H, d), 7.28 (2H, d), 8.33 (1H, s), 9.28 (1H, s), 9.52 (1H, s); m/z 222 (NH⁺).

Method F

Reference Example 6

4-(4-Hydroxyanilino)-6-(2-chloro-5-methylanilino) pyrimidine

The title compound was prepared in a similar manner to that of Reference Example 4 from 4-(4-hydroxyanilino)-6-chloropyrimidine (Reference Example 5) by reaction with 2-chloro-5-methylaniline in butan-1-ol in the presence of catalytic concentrated hydrochloric acid. The mixture was heated at reflux for 18 hours, concentrated and the residue purified by column chromatography eluting with DCMN-:MeOH: concentrated ammonia (94:5:1). Yield 84%. NMR: 2.26 (3H, s), 5.85 (1H, s), 6.68 (2H, d), 6.93 (1H, d), 7.19 (2H, d), 7.32 (1H, d), 7.46 (1H, s), 8.09 (1H, s), 8.44 (1H, s), 8.69 (1H, s), 9.11 (1H, s); m/z 327 (MH⁺).

Example 3

4-{4-[3-(N,N-Dimethyl)amino-2-hydroxypropoxy] anilino}-6-[N-(2-cyanoethyl)-2,5-dichloroanilino] pyrimidine To a solution of 4-{4-[2,3-epoxypropoxy]anilino}-6-[N-(2-cyanoethyl)-2,5-dichloroanilino]pyrimidine (Reference Example 7, 396 mg) in DMF (2 ml) was added dimethylamine (2M in MeOH, 3.5 ml) and the reaction stirred for 6 hours. The mixture was poured into water and extracted with EtOAc. The organic extract was dried (MgSO₄) and evaporated. The residue was purified by column chromatography eluting with DCM:MeOH:concentrated ammonia; 91:8:1 to give the product (366 mg, 84%) as a colourless oil. NMR: 2.15 (6H, s), 2.20–2.42 (2H, m), 2.84 (2H, m), 3.72–4.22 (5H, m), 4.77 (1H, d), 5.27 (1H, s), 6.81 (2H, d), 7.37 (2H, d), 7.56 (1H, dd), 7.76 (2H, m), 8.22 (1H, s), 8.88 (1H, s); m/z 501 (MH⁺).

Examples 4–7

The following compounds were prepared by an analogous method to that described in Example 3 using the appropriate N-alkylated epoxide starting material of Formula G (prepared by the procedure of Method G and the corresponding Reference Examples 7 and 8—see below).

Formula A

| Ex No | R₁ | R₂ | NMR | M/z (MH⁺) |
|---|---|---|---|---|
| 4† | 2,5-diCl | —CH₂C≡CH | 2.19(6H, s), 2.20–2.42(2H, m), 3.13–3.22(1H, m), 3.72–3.95 (3H, m), 4.50–4.80(3H, m), 5.41(1H, s), 6.81(2H, d), 7.39(2H, d), 7.50–7.75(3H, m), 8.22(1H, s), 8.94(1H, s) | 486 |
| 5 | 2,5-diCl | —CH₂Ph | 2.14–2.39(8H, m), 3.73–3.94(3H, m), 4.72(1H, m), 5.07(2H, brs), 5.36(1H, s), 6.79(2H, d), 7.17–7.46(9H, m), 7.62(1H, d), 8.21(1H, s), 8.85(1H, s) | 538 |
| 6† | 2,5-diCl | —CH₂CN | 2.19(6H, s), 2.21–2.42(2H, m), 3.73–3.92(3H, m), 4.77(1H, s), 4.91(2H, s), 5.39(1H, s), 6.81(2H, d), 7.39(2H, d), 7.60(1H, dd), 7.70(1H, m), 7.78(1H, d), 8.32(1H, s), 9.00(1H, s) | 487 |
| 7†,* | 2,4-diF | —CH₂CH₂F | 2.18(6H, s), 2.20–2.40(2H, m), 3.71–3.90(3H, m), 4.07(1H, t), 4.18(1H, t), 4.53(1H, t), 4.67(1H, t), 4.74(1H, m), 5.40(1H, s), 6.80(2H, d), 7.21(1H, t), 7.38(2H, d), 7.40–7.59(2H, m), 8.19(1H, s), 8.80(1H, s) | 462 |

†No DMF was used.
*Starting Material is Reference Example 8

Example 8

4-{4-[3-(N,N-Dimethyl)amino-2-hydroxypropoxy] anilino}-6-[N-(4-methoxybenzyl)-2,5-dichloroanilino]pyrimidine To a solution of 4-{4-[2,3-epoxypropoxy]anilino}-6-(2,5-dichloroanilino)pyrimidine (Reference Example 9; 316 ma) in DMF (3 ml) was added potassium tert-butoxide (1M solution in tetrahydrofuran. 0.86 ml) at −35° C. and the solution stirred for 30 minutes. 4-Methoxybenzyl bromide (0.32 ml) was then added and the solution allowed to warm to ambient temperature over 2.5 hours. After stirring for 1 hour at ambient temperature, dimethylamine (2M in MeOH, 2 ml) was added and the reaction stirred for a further 18 hours. The solution was then poured into water and extracted with EtOAc. The organic extract was dried (MgSO₄) and evaporated. The residue was purified by column chromatography eluting with DCM:MeOH:concentrated ammonia; 91:8:1 to give the title compound (220 mg, 49%) as a colourless oil. NMR: 2.19 (6H, s), 2.21–2.40 (2H, m), 3.68–3.92 (6H, m), 4.76 (1H, m), 4.95 (2H, brs), 5.38 (1H, s), 6.81 (4H, m), 7.19 (2H, m), 7.35 (3H, m), 7.42 (1H, dd), 7.61 (1H; d), 8.21 (1H, s), 8.83 (1H, s); m/z 568 (MH$^+$).

Examples 9–11

The following compounds of Formula A were prepared by the method of Example 8 using the appropriate un-N-alkylated epoxides of Formula H (prepared by the procedure of Method H and the corresponding Reference Example 9—see below) and the appropriate bromo-substituted alkylating agent (apart from Example 9 in which 1-(3-bromopropyl)-2,2,5,5-tetramethyl-1-aza-2,5-disilacylopentane (97%) was used as the alkylating agent, and which hydrolysed under the reaction conditions to give the $R_2$=—$CH_2CH_2CH_2NH_2$ product).

| Ex No | $R_1$ | $R_2$ | NMR | M/z (MH$^{+}$) |
|---|---|---|---|---|
| 9 | 2,5-diCl | —$CH_2CH_2CH_2NH_2$ | 1.40–1.70 (4H, m), 2.19–2.42 (8H, m), 2.56 (2H, t), 3.71–3.98 (5H, m), 4.75 (1H, s), 5.38 (1H, s), 6.81 (2H, d), 7.39 (2H, d), 7.49 (1H, dd), 7.60 (1H, m), 7.67 (1H, d), 8.18 (1H, s), 8.80 (1H,s) | 505 |
| 10 | 2,5-diCl | —$CH_2CH_2CH_2CF_3$ | 1.78 (2H, m), 2.19 (6H, s) 2.21–2.44 (4H, m), 3.71–3.96 (5H, m), 4.76 (1H, m), 5.24 (1H, s), 6.80 (2H, d), 7.38 (2H, d), 7.52 (1H, dd), 7.71 (2H, m), 8.20 (1H, s), 8.80 (1H, s) | 558 |
| 11 | 2,5-diCl | —$CH_2CH$=$CHBr$* | 2.20–2.44 (8H, m), 3.71–3.96 (3H, m), 4.30–4.68 (2H, m), 4.77 (1H, s), 5.37 (1H, s), 6.28–6.60 (2H, m), 6.83 (2H, d), 7.39 (2H, d), 7.52 (1H, m), 7.71 (2H, m), 8.21 (1H, s), 8.87 (1H, s) | 566 |

*Mixture of E- and Z- isomers

Example 12

4-{4-[3-(N,N-Dimethyl)amino-2-hydroxyoropoxy]anilino}-6-(N-cyanomethyl-2,4-difluoroanilino)pyrimidine The title compound was made by the procedure of Example 1 (using 4-(4-hydroxyanilino)-6-(N-cyanomethyl-2,4-difluoroanilino)pyrimidine as a starting material (prepared by an analogous procedure to Reference Examples 1–4 and using the appropriate aniline). Yield: 131 mg, 46%. NMR: 2.18 (6H, s), 2.20–2.40 (2H, m), 3.73–3.92 (3H, m), 4.74 (1H, d), 5.49 (1H, s), 6.83 (1H, d), 7.28 (1H, m), 7.37 (2H, d), 7.49–7.64 (2H, m), 8.32 (1H, s), 8.98 (1H, m): m/z 455 (MH$^+$).

Preparation of Starting Materials for Examples 3–12

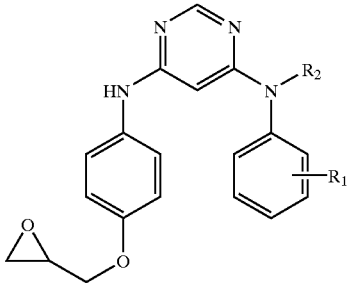

Formula G

Method G

The starting materials for the above Examples are readily prepared and isolated by standard methods. The following reactions (Reference Examples 7 and 8) are illustrations of the preparation of the N-alkylated epoxide starting materials of Formula G used in the above reactions.

Reference Example 7

4-{4-[2,3-Epoxypropoxy]anilino}-6-[N-(2-cyanoethyl)-2,5-dichloroanilino]pyrimidine To a solution of 4-{4-[2,3-epoxypropoxy]anilino}-6-(2,5-dichloroanilino)pyrimidine (Reference Example 9, 1.4 g) in DMSO (3.75 ml) was added $K_2CO_3$ (1.1 g) and 3-bromopropionitrile (0.66 ml) and the reaction stirred for 20 hours. The mixture was poured into water and extracted with EtOAc. The organic extract was dried (MgSO$_4$) and evaporated. The residue was purified by column chromatography eluting with DCM:MeOH; 99:1 to give the product (436 mg, 26%) as a colourless oil. NMR: 2.66 (1H, t), 2.78–2.92 (3H, m), 3.76 (1H, dd), 3.82–4.36 (3H, m), 5.28 (1H, s), 6.82 (2H, d), 7.38 (2H, d), 7.57 (1H, dd), 7.72 (1H, m), 8.25 (1H, s), 8.89 (1H, s); m/z 456(MH$^+$).

Reference ExamDle 8

4-[4-(2,3-Epoxypropoxy)anilino]-6-[N-(2-fluoroethyl)-2,4-difluoroanilino]pyrimidine To a solution of 4-[4-(2,3-epoxypropoxy)anilino]-6-(2,4-difluoroanilino)pyrimidine (prepared by an analogous procedure to Reference Examples 9 and using the appropriate aniline) (1.4 g) in DMF (11 ml) at 0° C. was added sodium tert-butoxide (580 mg) and the mixture stirred for 10 minutes. To a portion of this solution (2.2 ml) was added 1-bromo-2-fluoroethane (0.11 ml) and the reaction stirred for 1 hour. The solution was then poured into water and extracted with EtOAc. The organic extract was dried (MgSO$_4$) and evaporated. The residue was purified by column chromatography eluting with DCM:MeOH; 125:2 to give the product (237 mg, 75%) as a colourless oil. NMR: 2.65 (2H, m), 2.81 (2H, m), 3.79 (1H, dd), 4.01–4.18 (2H, m), 4.51 (2H, t), 4.67 (2H, t), 5.40 (1H, s), 6.82 (2H, d), 7.21 (1H, m), 7.30–7.59 (4H, m), 8.20 (1H, s), 8.84 (1H, s).

Method H

Un-N-alkylated epoxides of Formula H may be obtained by reaction of 4,6-dichloropyrimidine:
 a) with 4-hydroxyaniline (see Reference Example 5), then
 b) reaction with the relevant ($R_1$ substituted)aniline (see Reference Example 4), then
 c) formation of the epoxide with epibromhydrin (see Reference Example 9).

Alternatively, steps a) and b) may be reversed.

The starting materials for the above Examples are readily prepared and isolated by standard methods. The following reaction (Reference Example 9) illustrates the preparation of the un-N-alkylated epoxide starting materials of Formula H used in the above reactions.

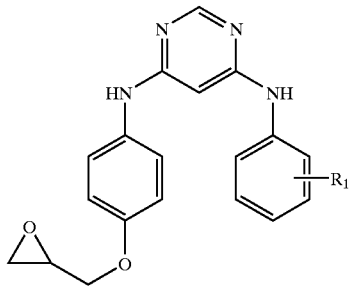

Formula H

Reference Example 9

4-{4-[2,3-Epoxyproxy]anilino}-6-(2,5-dichloroanilino)pyrimidine

To a solution of 4-(4-hydroxyanilino)-6-(2,5-dichloroanilino)pyrimidine (prepared by analogy to Reference Example 6 using the appropriate aniline; 2.83 g) and powdered $K_2CO_3$ (2.25 g) in DMSO was added epibromohydrin (0.98 ml) and the reaction stirred for 21 hours. The solution was poured into water and extracted with EtOAc. The organic extract was washed with brine, dried ($MgSO_4$) and evaporated over silica. The residue was purified by column chromatography eluting with DCM:MeOOH; 50:1 to give the title compound (2.76 g, 84%) as a white solid. NMR: 2.69 (1H, dd), 2.83 (1H, dd), 3.31 (1H, m), 3.80 (1H, dd), 4.28 (1H, dd), 6.15 (1H, s), 6.92 (2H, d), 7.13 (1H, dd), 7.38 (2H, d), 7.48 (1H, d), 8.00 (1H, m), 8.20 (1H, s), 8.71 (1H, s), 8.99 (1H, s); m/z 403 (MH$^+$).

Examples 13–14

The following compounds of Formula A were prepared by an analogous method to that described in Example 1 using the appropriate 4-hydroxy compounds (see Reference Examples 10 and 11 below).

| Ex No | R$_1$ | R$_2$ | NMR (300 MHz) | M/z (MH$^{+}$) |
|---|---|---|---|---|
| 13 | 2,4-diF | CH$_3$ | 2.14 (s, 6H), 2.25 (m, 1H), 2.36 (m, 1H), 3.26 (s, 3H), 3.82 (m, 3H), 4.73 (d, 1H), 5.52 (s, H), 6.82 (d, 2H), 7.18 (t, 1H), 7.37 (d, 2H), 7.43 (dd, 1H), 7.50 (m, 1H), 8.14 (s, 1H), 8.82 (s, 1H) | 430.4 |
| 14 | 2-CH$_3$ | —CH$_2$CH$_2$OH | 2.09 (s, 3H), 2.19 (s, 6H), 2.31 (dd, 1H), 2.41 (dd, 1H), 3.58 (brs, 3.H), 3.78 (m, 1H), 3.88 (m, 2H), 4.07 (brs, 1H), 4.71 (brs, 1H), 4.80 (brs, 1H), 5.17 (brs, 1H), 6.79 (d, 2H), 7.31 (m, 6H), 8.18 (s, 1H), 8.70 (s, 1H) | 438.6 |

Preparation of Starting Materials for Examples 13 and 14

The starting materials of Formula I for Examples 13 and 14 were prepared using the procedure of Reference Examples 4 or 6 using the appropriate aniline.

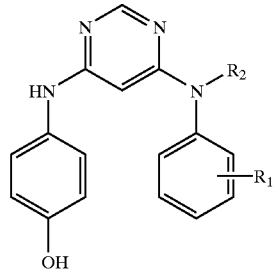

Formula I

| Ref Ex | Method of Ref Ex | R$_1$ | R$_2$ | NMR | M/z (MH$^+$) |
|---|---|---|---|---|---|
| 10 | 4* | 2,4-diF | CH$_3$ | 3.26(s, 3H), 5.48(s, 1H), 6.64(d, 2H), 7.16(t, 1H), 7.20(d, 2H), 7.46(m, 2H), 8.11(s, 1H), 8.69(s, 1H), 9.02(s, 1H). | 329.3 |
| 11 | 6 | 2-CH$_3$ | —CH$_2$CH$_2$OH | 2.07(s, 3H), 3.56(bs, 3H), 4.69(t, 2H), 5.09(bs, 1H), 6.58(d, 2H), 7.14(d, 2H), 7.28(m, 4H), 8.12(s, 1H), 8.54(s, 1H), 8.96(s, 1H). | 337.4 |

*1,2-dichlorobenzene was used as solvent

Example 15

4-[4-(3-t-Butylamnino-2-hydroxyprorpoxy)anilino]-6-[(N-4,4,4-trifluorobutyl)-2-chloro-5-methylanilino]pyrimidine 4-(4-Hydroxyanilino)-6-[(N-4,4,4-trifluorobutyl)-2-chloro-5-methylanilino]pyrimidine (Reference Example 14, 250 mg, 0.57 mmol) was dissolved in DMSO (2 ml) and $K_2CO_3$ (160 mg, 1.15 mmol) was added. The resulting suspension was stirred for 30 mins to give a turquoise solution. Epibromohydrin (0.15 ml, 1.7mmol) was added and stirred the solution was stirred overnight. To this green solution was added t-butylamine (1.21 ml, 11.4 mmol) and the reaction was stirred for 12 hours. DCM (20 ml) and silica (3 g) were added. The mixture was evaporated to dryness on high vacuum and then loaded onto a 10 g Mega Bond Elut column. Eluted with DCM (2×25 ml), 2% $NH_3$ in MeOH (3×25 ml), 4% $NH_3$ in MeOH (3×25 ml), 6% $NH_3$ in MeOH (3×25 ml), 10% $NH_3$ in MeOH (9×25 ml) and product was isolated as a pink/brown oil (280 mg, 86%). M/z 566.7 (MH$^+$).

Example 16

4-[4-(3-Isopropylamino-2-hydroxypropoxy)anilino]-6-(N-4,4,4-trifluorobutyl-2-chloro-5-methylanilino)pyrimidine The title compound was prepared by the method of Example 15 except that isopropylamine (0.98 ml, 11.5 mmol) was used instead of t-butylamine to give a pink/brown oil (270 mg, 85%), M/z 552.7 (MH$^+$).

Reference Example 12

4-Chloro-6-(2-chloro-5-methylanilino)pyrimidine

Tetramethylene sulphone (10 ml) was added to 4,6-dichloropyrimidine (25.0 g, 170 mmol) and heated to 125° C. 2-Chloro-5-methylaniline (11.90 g, 84 mmol) was added portion wise over 20 mins. The reaction mixture was heated at 125° C. for 2 hours. The reaction was allowed to cool to room temperature and DCM (200 ml) was added. The mixture was basified to pH 9–10 with methanolic ammonia and evaporated onto silica (15 g). The residue was purified by column chromatography eluting with EtOAc:isohexane (10:90) to give a white solid (12.25 g, 29%). NMR (300 MHz): 2.3 (s, 3H), 6.7 (s, 1H), 7.0 (d, 1H), 7.4 (d, 1H), 7.5 (s, 1H), 8.4 (s, 1H), 9.4 (s, 1H); m/z 254 (MH$^+$).

Reference Example 13

4-Chloro-6-[(N-4,4,4-Trifluorobutyl)-2-chloro-5-methylanilino]pyrimidine

4-Chloro-6-(2-chloro-5-methylanilino)pyrimidine (Reference Example 12, 12.00 g, 47 mmol) was dissolved in NMP (3 ml) and potassium carbonate (13.11 g, 95 mmol) and 1,1,1-trifluorobutane (11.77 g, 62 mmol) were added. The reaction mixture was heated at 50° C. for 3 hours the allowed to cool to room temperature. DCM (10 ml) was added and the mixture was evaporated onto silica (2 g). The residue was purified by column chromatography eluting with EtOAc: iso-hexane (10:90) to give a colourless oil (14.14 g, 82%). NMR: 1.8 (m, 2H), 2.3 (m, 5H), 3.8 (brs, 1H), 4.0 (brs, 1H), 7.2 (d, 1H) 7.4 (s, 1H), 7.6 (d, 1H), 8.4 (brs, 1H); m/z 364.2 (MH$^+$).

Reference Example 14

4-(4-Hydroxyanilino)-6-[(N-4,4,4-trifluoroburyl)-2-chloro-5-methylanilino]pyrimidine 4-Chloro-6-[(N-4,4,4-trifluorobutyl)-2-chloro-5-methylanilino]pyrimidine (Reference Example 13, 7.00 g, 19 mmol) was suspended in tetramethylene sulphone (15 ml) and p-aminophenol was added (2.0 g, 18 mmol). The reaction mixture was heated at 160° C. for 90 mins and allowed to cool to room temperature. DCM (50 ml) and silica (10 g) were added and the mixture was evaporated to dryness. Purified by MPLC, eluting with DCM, then 2% NH$_3$ in MeOH to isolate product as white solid (6.51 g, 77%). NMR (300 MHz) 1.8 (m, 2H), 2.2–2.4 (m, 5H), 5.2 (s, 1H), 6.6 (d, 2H), 7.2 (d, 2H), 7.3 (d, 1H), 7.35 (s, 1H), 7.5 (d, 1H), 8.2 (s, 1H), 8.6 (s, 1H), 9.0 (s, 1H); m/z 437.3 (MH$^+$).

Example 17

4-{4-[3-(N,N-Dimethyl)amino-2-hydroxyproyoxy]anilino}-6-(N-cinnamyl-4-bromoanilino)pyrimidine 4-Chloro-6-[N-cinnamyl-4-bromoanilino]pyrimidine (Reference Example 16, 0.38 g, 0.95 mmol) was dissolved in a mixture of NMP (1 ml) and tetramethylene sulphone (1 ml). 4-[3-(N,N-Dimethyl)amino-2-hydroxypropoxy]aniline dihydrochloride (Reference Example 21) (0.26 g, 0.92 mmol) was added and the mixture heated to 160° C. for one hour. After cooling to ambient temperature the brown solution was partitioned between EtOAc and saturated aqueous sodium bicarbonate solution. The organic layer was washed once with 50% aqueous brine and once with saturated brine. It was then dried over anhydrous sodium sulphate, filtered and evaporated. The residue was purified by column chromatography [7M NH$_3$/MeOH (4%): DCM]. Fractions containing product were evaporated and the residual gum dissolved in ether. This solution was filtered and evaporated to give a foam (0.31 g, 57%). NMR: 2.15 (s, 6H), 2.2–2.4 (m, 2H), 3.7–3.9 (m, 3H), 4.65 (d, 2H), 4.74 (d, 1H), 5.60 (s, 1H), 6.25–6.5 (m, 2H), 6.8 (d, 2H), 7.16–7.4 (m, 9H), 7.63 (d, 2H), 8.2 (s, 1H), 8.8 (s, 1H); m/z 574 [MH$^+$].

Examples 18–22

The following compounds were prepared by an analogous method to that described in Example 17 using the appropriate starting materials. The starting materials for Examples 18–20 were prepared by analogy with Reference Example 16, the starting materials for Examples 21 and 22 are described in Reference Examples 17 and 18.

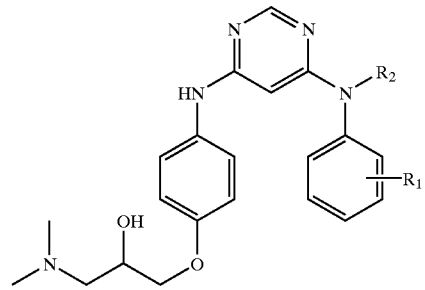

Formula A

| Ex No | R$_1$ | R$_2$ | NMR 300 MHz | m/z (MH$^+$) |
|---|---|---|---|---|
| 18 | 2,5-diCl | Ph—CH=CH—CH$_2$— | 2.16(s, 6H), 2.2–2.4(m, 2H), 3.76(m, 1H), 3.85(m, 2H), 4.6(brs, 2H), 4.74(d, 1H), 5.42(brs, 1H), 6.35(m, 1H), 6.5(d, 1H), 6.8(d, 2H), 7.3(m, 7H), 7.47(dd, 1H), 7.66(m, 2H), 8.2(s, 1H), 8.85(s, 1H), | 564 |

-continued

Formula A

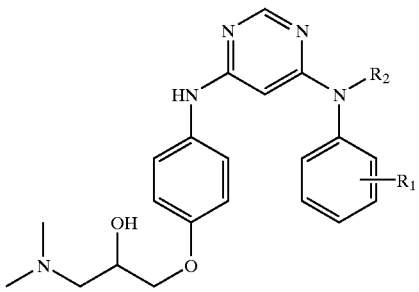

| Ex No | R₁ | R₂ | NMR 300 MHz | m/z (MH⁺) |
|---|---|---|---|---|
| 19 | 2-Cl-4-Me | Ph—CH=CH—CH₂— | 2.15(s, 6H), 2.2–2.4(m, 5H), 3.7–3.9(m, 3H), 4.3(brs, 1H), 4.72(brs, 1H), 4.85(brs, 1H), 5.28(brs, 1H), 6.25–6.49(m, 2H), 6.78(d, 2H), 7.15–7.4(m, 9H), 7.46(s, 1H), 8.2(s, 1H), 8.8(s, 1H) | 544 |
| 20 | 2,4-diF | Ph—CH=CH—CH₂— | 2.16(s, 6H), 2.2–2.4(m, 2H), 3.77(m, 1H), 3.90(m, 2H), 4.57(d, 2H), 4.72(brs, 1H), 5.50(s, 1H), 6.24–6.36(m, 1H), 6.47(d, 1H), 6.8(d, 2H), 7.14–7.46(m, 9H), 7.53(m, 1H), 8.18(s, 1H), 8.82(s, 1H) | 532 |
| 21 | 2-Cl-5-Me | CF₃—(CH₂)₃— | 1.76(m, 2H), 2.15(s, 6H), 2.2–2.4(m, 7H), 3.7–4.1(m, 5H), 4.72(brs, 1H), 5.18(s, 1H), 6.78(d, 2H), 7.24(dd, 1H), 7.34(m, 3H), 7.53(d, 1H), 8.20(s, 1H), 8.77(s, 1H) | 538 |
| 22* | 2-Cl-5-Me | Br—CH=CH—CH₂— | 2.16(s, 6H), 2.2–2.4(m, 5H), 3.7–3.9(m, 3H), 4.73(brs, 1H), 5.26(brs, 1H), 6.26–6.54(m, 2H), 6.78(d, 2H), 7.2–7.37(m, 4H), 7.50(d, 1H), 8.20(s, 1H), 8.80(s, 1H) | 546 |

*The reaction was carried out at 100° C. for four hours.

Reference Example 15

4-Chloro-6-(4-bromoanilino)pyrimidine 4,6-Dichloropyrimidine (3.0 g, 20 mmol) was mixed with 4-bromoaniline (3.3 g, 19 mmol) and heated to 125° C. for two hours in tetramethylene sulphone. After cooling the reaction mixture was partitioned between saturated aqueous sodium bicarbonate solution and EtOAc. The organic portion was washed, dried over sodium sulphate, filtered and evaporated. The residue was purified by column chromatography (EtOAc (20%): isohexane) to yield a solid (0.6 g, 11%). M/z 284 (MH)⁺.

Reference Example 16

4-Chloro-6-(N-cinnamyl-4-bromoanilino)pyrimidine

4-Chloro-6-(4-bromoanilino)pyrimidine (Reference Example 15) (0.3 g, 1.0 mmol) and cinnamyl bromide (0.23 g, 1.2 mmol) were dissolved in NMP (2 ml). Caesium carbonate (0.5 g, 1.5 mmol) was added and the mixture was heated to 70° C. for one hour. Following an aqueous work-up with extraction into EtOAc the product was obtained by column chromatography (EtOAc (4%): isohexane) (0.4 g, 94%). M/z 400 (NH)⁺.

Reference Example 17

4-Chloro-6-[N-(4,4,4-trifluorobutyl)-2-chloro-5-methylanilino]pyrimidine

4-Chloro-6-(2-chloro-5-methylanilino)pyrimidine (Reference Example 12) (0.28 g, 1.1 mmol) and 1,1,1-trifluoro-4-bromobutane (0.32 g, 1.67 mmol) were dissolved in NMP (2 ml). Anhydrous potassium carbonate (0.31 g, 2.2 mmol) was added and the mixture heated to 50° C. for three hours. Following an aqueous work-up the product was obtained by column chromatography on silica gel using EtOAc-isohexane mixtures. (0.3 g, 75%). M/z 364 (MH)⁺.

Reference Example 18

4-Chloro-6-[N-(3-bromoallyl)-2-chloro-5-methylanilino]pyrimidine

4-Chloro-6-(2-chloro-5-methylanilino)pyrimidine (Reference Example 12) (0.5 g, 1.97 mmol) and 1,3-dibromopropene [cis/trans mixture] (0.6 g, 3.0 mmol) were dissolved in NMP (2 ml). Anhydrous potassium carbonate (0.54 g, 4 mmol) was added and the mixture stirred at room temperature for seventeen hours. After aqueous work-up the product was obtained by column chromatography on silica gel using EtOAc/isohexane mixtures (0.68 g, 93%). M/z 372 (MH)⁺.

Reference Example 19

1-(4-Nitrophenoxy)-2,3-epoxypropane 1-(4-Nitrophenoxy)-2,3-epoxypropane was prepared by an analogous method to that described by Zhen-Zhong Lui et. al. in Synthetic Communications (1994), 24, 833–838.

4-Nitrophenol (4.0 g), anhydrous potassium carbonate (8.0 g) and tetrabutylamnnonium bromide (0.4 g) were mixed with epibromohydrin (10 ml). The reaction mixture was heated at 100° C. for 1 hour. After cooling to ambient temperature, the reaction mixture was diluted with EtOAc and filtered. The filtrate was evaporated to dryness and the residue was co-distilled twice with toluene. The resulting oil was purified by column chromatography and eluted with EtOH (1.0%):DCM to give the title product on evaporation as an oil that crystallised (4.36 g, 77.7%). NMR (CDCl$_3$, 300 MHz): 2.78 (m, 1H), 2.95 (m, 1H), 3.38 (m, 1H), 4.02 (dd, 1H), 4.38 (dd, 1H), 7.00 (d, 2H), 8.20 (d, 2H); m/z: (ES$^+$) 196 (MH$^+$).

Reference Example 20

3-(N,N-Dimethyl)amino-2-hydroxy-1-(4-nitrophenoxy)propane 1-(4-Nitrophenoxy)-2,3-epoxypropane (Reference Example 19, 4.3 g) was dissolved in methanol (30 ml) and DMF (10 ml). Dimethylamine (2M solution in methanol, 17 ml) was added and the mixture was stirred at ambient temperature overnight. The reaction mixture was evaporated to dryness and the residue was dissolved in saturated sodium bicarbonate solution and EtOAc. The EtOAc layer was separated and washed twice with saturated brine, dried over anhydrous sodium sulphate, filtered and evaporated to give the title product as an oil that slowly crystallised under high vacuum (4.79 g, 89.9%). NMR (CDCl$_3$, 300 MHz): 2.33 (s, 6H), 2.98 (m, 1H), 2.54 (m, 1H), 4.00 (m, 3 H), 7.00 (d, 2H), 8.20 (d, 2H); m/z: (ES$^+$) 241 (MH$^+$).

Reference Example 21

4-[3-(N,N-Dimethyl)amino-2-hydroxyoroloxy]aniline 3-(N,N-Dimethyl)amino-2-hydroxy-3-(4-nitrophenoxy)propane (Reference Example 20, 3.75 g) was dissolved in EtOH (40 ml). Under an atmosphere of nitrogen, 10% palladium-on-carbon (0.4 g) was added. The nitrogen atmosphere was replaced by one of hydrogen and the reaction mixture was stirred overnight. The catalyst was removed by filtration through diatomaceous earth and the filtrate was evaporated to dryness. The residue was dissolved in diethyl ether containing a small amount of isopropanol and hydrogen chloride solution (1M in ether, 16 ml) was added. The ether was evaporated and the solid residue was suspended in isopropanol. This mixture was heated on a steam bath for several minutes then allowed to cool to ambient temperature. The resulting powder was collected by filtration, washed with isopropanol, ether and dried to give the title product (3.04 g, 72.4%). NMR (300 MHz): 2.80 (s, 6H), 3.15 (m, 2H), 3.88 (m, 2H), 4.25 (m, 1H), 5.93 (br S, 1H), 6.88 (m, 4H); m/z: (ES$^+$) 211 (MH$^+$); EA: C$_{11}$H$_{13}$N$_2$O$_2$.1.6 HCl requires C; 49.2, H; 7.4, N; 10.4, Cl; 21.7%: found: C; 49.2, H; 7.2, N; 10.1; Cl; 19.1%.

Example 23

The following illustrate representative pharmaceutical dosage forms containing the compound of formula (I), or a pharmaceutically-acceptable salt or in-vivo hydrolysable ester thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph. Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:
1. A pyrimidine compound of the formula (I)

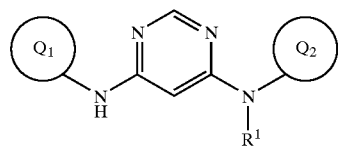

wherein
R$^1$ is selected from (1–6C)alkyl [substituted by one or two substituents independently selected from halo, amino, (1–4C)alkylamino, di-[(1–4C)alkyl]amino, hydroxy, cyano, (1–4C)alkoxy, (1–4C)alkoxycarbonyl, carbamoyl, —NHCO(1–4C)alkyl, trifluoromethyl, phenylthio, phenoxy, pyridyl, morpholino], benzyl, 2-phenylethyl, (3–5C)alkenyl [optionally substituted by up to three halo substituents, or by one trifluoromethyl substituent, or one phenyl substituent], N-phthalimido-(1–4C)alkyl, (3–5C)alkynyl [optionally substituted by one phenyl substituent] and (3–6C)cycloalkyl-(1-6C)alkyl;

wherein any phenyl or benzyl group in R¹ is optionally substituted by up to three substituents independently selected from halogeno, hydroxy, nitro, amino, (1–3C)alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C)alkyl]amino, hydroxy and trifluoromethyl], (3–5C)alkenyl [optionally substituted by up to three halo substituents, or by one trifluoromethyl substituent], (3–5C)alkynyl, (1–3C)alkoxy, —SH, —S-(1–3C)alkyl, carboxy, (1–3C)alkoxycarbonyl;

$Q_1$ and $Q_2$ are independently selected from phenyl, naphthyl, indanyl and 1,2,3,4-tetrahydronaphthyl;

and one or both of $Q_1$ and $Q_2$ bears on any available carbon atom bne substituent of the formula (Ia) and $Q_2$ may optionally bear on any available carbon atom further substituents of the formula (Ia)

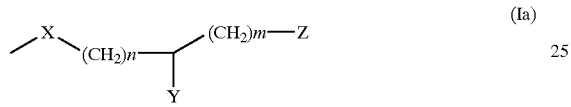

(Ia)

[provided that when present in $Q_1$ the substituent of formula (Ia) is not adjacent to the —NH— link];
wherein
X is $CH_2$, O, S, NH or NRx [wherein Rx is (1–4C)alkyl, optionally substituted by one substituent selected from halo, amino, cyano, (1–4C)alkoxy or hydroxy];

Y is H or as defined for Z;

Z is OH, SH, $NH_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;

n is 1, 2 or 3; m is 1, 2 or 3;

and $Q_1$ and $Q_2$ may each optionally and independently bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, 2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido ($H_2$N—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or in addition to, the above optional substituents, $Q_1$ and/or $Q_2$ may optionally bear on any available carbon atom up to two further substituents independently selected from (3–8C)cycloalkyl, phenyl-(1–4C)alkyl, phenyl-(1–4C)alkoxy, phenylthio, phenyl, naphthyl, benzoyl, phenoxy, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C)alkoxy substituents may optionally bear up to five substituents independently selected from halogeno, (1–4C)alkyl and (1–4C)alkoxy; or a pharmaceutically-acceptable salt or in-vivo-hydrolysable ester thereof.

2. A pyrimidine compound of the formula (I) as claimed in claim 1,
wherein
R¹ is benzyl [optionally substituted by up to three substituents independently selected from halogeno, hydroxy, nitro, amino, (1–3C)alkylamino, di-[(1–3C)alkyl]amino, cyano, trifluoromethyl, (1–3C)alkyl, (1–3C)alkoxy, —SH, —S-(1–3C)alkyl, carboxy and (1–3C)alkoxycarbonyl], (3–5C)alkynyl, (3–6C)cycloalkyl-(1–6C)alkyl, (1–4C)alkyl [substituted by one or two substituents independently selected from hydroxy, amino, halo, trifluoromethyl and cyano] or (3–5C)alkenyl substituted by one to three halo groups or one phenyl substituent;

$Q_1$ and $Q_2$ are independently selected from phenyl, naphthyl, indanyl and 1,2,3,4-tetrahydronaphthyl;

and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];

X is $CH_2$, O, S, NH or NRx [wherein Rx is (1–4C)alkyl, optionally substituted by one substituent selected from halo, amino, cyano, (1–4C)alkoxy or hydroxy];

Y is H or as defined for Z;

Z is OH, SH, $NH_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;

n is 1, 2 or 3; m is 1, 2 or 3;

and $Q_1$ and $Q_2$ may each optionally and independently bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino-(1–3C)alkyl, (1–4C) alkylamino-(1–3C)alkyl, di-[(1–4C)alkyl]amino-(1–3C)alkyl, cyano-(1–4C)alkyl, (2–4C) alkanoyloxy-(1–4C)-alkyl, (1–4C)alkoxy-(1–3C) alkyl, carboxy-(1–4C)alkyl, (1–4C)alkoxycarbonyl-(1–4C)alkyl, carbamoyl-(1–4C)alkyl, N-(1–4C) alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkoxy, cyano-(1–4C)alkoxy, carbamoyl-(1–4C)alkoxy, N-(1–4C) alkylcarbamoyl-(1–4C)alkoxy, N,N-di-[(1–4C) alkyl]-carbamoyl-(1–4C)alkoxy, 2-aminoethoxy, 2-(1–4C)alkylaminoethoxy, 2-di-[(1–4C)alkyl] aminoethoxy, (1–4C)alkoxycarbonyl-(1–4C)alkoxy, halogeno-(1–4C)alkoxy, 2-hydroxyethoxy, (2–4C) alkanoyloxy-(2–4C)alkoxy, 2-(1–4C)alkoxyethoxy, carboxy-(1–4C)alkoxy, (3–5C)alkenyloxy, (3–5C) alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C) alkylsulphonyl, ureido (H$_2$N—CO—NH—), (1–4C) alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or in addition to, the above optional substituents, $Q_1$ and/or $Q_2$ may optionally bear on any available carbon atom up to two further substituents independently selected from (3–8C) cycloalkyl, phenyl-(1–4C)alkyl, phenyl-(1–4C)alkoxy, phenylthio, phenyl, naphthyl, benzoyl, phenoxy, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C) alkoxy substituents may optionally bear up to five substituents independently selected from halogeno, (1–4C)alkyl and (1–4C)alkoxy;

or a pharmaceutically-acceptable salt or in-vivo-hydrolysable ester thereof.

3. A pyrimidine compound of the formula (I) as claimed in claim 1,
wherein
$R^1$ is benzyl [optionally substituted by one (1–3C) alkoxy substituent], (3–5C)alkynyl, (3–6C) cycloalkyl-(1–6C)alkyl, (1–4C)alkyl [substituted by one or two substituents independently selected from hydroxy, amino, halo, trifluoromethyl and cyano] or (3–5C)alkenyl substituted by one to three halo groups or one phenyl substituent;
$Q_1$ and $Q_2$ are independently selected from phenyl or indanyl;
and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];
X is CH$_2$, O, S, NH or NRx [wherein Rx is (1–4C) alkyl, optionally substituted by one substituent selected from halo, amino, cyano, (1–4C)alkoxy or hydroxy];
Y is H or as defined for Z;
Z is OH, SH, NH$_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;
n is 1, 2 or 3; m is 1, 2 or 3;
and $Q_1$ may optionally bear on any available carbon atom up to four substituents independently selected from halogeno, thio, nitro, carboxy, cyano, (2–4C) alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;
and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino,
and also independently, or in addition to, the above optional substituents, $Q_2$ may optionally bear on any available carbon atom up to two further substituents independently selected from phenylthio, phenyl, phenoxy and benzimidazol-2-yl;
or a pharmaceutically-acceptable salt or in-vivo-hydrolysable ester thereof.

4. A pyrimidine compound of the formula (I) as claimed in claim 1,
wherein
$R^1$ is benzyl [optionally substituted by one (1–3C) alkoxy substituent], (3–5C)alkynyl, (3–6C) cycloalkyl-(1–6C)alkyl, (1–4C)alkyl [substituted by one or two substituents independently selected from hydroxy, amino, halo, trifluoromethyl and cyano] or (3–5C)alkenyl substituted by one to three halo groups or one phenyl substituent;
$Q_1$ and $Q_2$ are independently selected from phenyl or indan-5-yl;
and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia)is not adjacent to the —NH— link];
X is O;
Y is H or OH;
Z is —NH(1–4C)alkyl, -N[(1–4C)alkyl]$_2$, —NH-(3–8C)cycloalkyl, pyrrolidin-1-yl or piperazin-1-yl [optionally substituted in the 4-position by (1–4C)alkyl or (1–4C)alkanoyl];
n is 1 or 2 and m is 1 or 2;
and $Q_1$ may optionally bear on any available carbon atom up to four substituents independently selected from halogeno, thio, nitro, carboxy, cyano, (2–4C) alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

5. A pyrimidine compound of the formula (I) as claimed in claim 1,
wherein
$R^1$ is cyanomethyl, —$CH_2CH$=$CHBr$, —$CH_2CH_2CH_2CF_3$ or —$CH_2CH$=$CH$-phenyl;
$Q_1$ and $Q_2$ are independently selected from phenyl or indan-5-yl; and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];
X is O;
Y is H or OH;
Z is —NH(1–4C)alkyl, —N[(1–4C)alkyl]$_2$, —NH-(3–8C)cycloalkyl, pyrrolidin-1-yl or piperazin-1-yl [optionally substituted in the 4-position by (1–4C)alkyl or (1–4C)alkanoyl];
n is 1 or 2 and m is 1 or 2;
and $Q_1$ and/or $Q_2$ may independently and optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_1$ and/or $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

6. A pyrimidine compound of the formula (I) as claimed in claim 1,
wherein
$R^1$ is cyanomethyl, —$CH_2CH$=$CHBr$, —$CH_2CH_2CH_2CF_3$ or —$CH_2CH$=$CH$—phenyl;
$Q_1$ and $Q_2$ are both phenyl;
$Q_1$ bears on any available carbon atom one substituent of the formula (Ia) [provided that the substituent of formula (Ia) is not adjacent to the —NH— link];
X is O;
Y is H or OH;
Z is —NH(1–4C)alkyl or —N[(1–4C)alkyl]$_2$;
n is 1 or 2and m is 1 or2;
and $Q_1$ and/or $Q_2$ may independently and optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_1$ and/or $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

7. A pyrimidine compound of the formula (I) as claimed in claim 1,
wherein
$R^1$ is cyanomethyl, —$CH_2CH$=$CHBr$, —$CH_2CH_2CH_2CF_3$ or —$CH_2CH$=$CH$-phenyl;
$Q_1$ and $Q_2$ are both phenyl;
$Q_1$ bears on any available carbon atom one substituent of the formula (Ia) [provided that the substituent of formula (Ia) is not adjacent to the —NH— link];
X is O;
Y is OH;
Z is —NH(1–4C)alkyl or —N[(1–4C)alkyl]$_2$;
n is 1 or 2 and m is 1 or 2;
and $Q_2$ optionally bears on any available carbon atom up to two substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C) alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;.

or a pharmaceutically-acceptable salt or in-vivo-hydrolysable ester thereof.

8. A pyrimidine compound of the formula (I) as claimed in claim 1, being:

4-{4-[3-(N,N-Dimethyl)amino-2-hydroxy-propoxy] anilino}-6-(N-cyanomethyl-2-bromo-4-methylanilino) pyrimidine;

4-{4-[3-(N,N-Dimethyl)amino-2-hydroxy-propoxy] anilino}-6-(N-cyanomethyl-2-chloro-5-methylanilino) pyrimidine;

4-{4-[3-(N,N-Dimethyl)amino-2-hydroxy-propoxy] anilino}-6-(N-cyanomethyl-2,5-dichloroanilino) pyrimidine;

4-{4-[3-(N,N-Dimethyl)amino-2-hydroxy-propoxy] anilino}-6-(N-(4,4,4-trifluorobutyl)-2,5-dichloroanilino)pyrimidine;

4-{4-[3-(N,N-Dimethyl)amino-2-hydroxy-propoxy] anilino}-6-(N-(3-phenylprop-2-enyl)-2,4-difluoroanilino)pyrimidine;

4-{4-[3-(N,N-Dimethyl)amino-2-hydroxy-propoxy] anilino}-6-(N-(3-phenylprop-2-enyl)-2-chloro-4-methylanilino)pyrimidine;

or a pharmaceutically-acceptable salt or in-vivo hydrolysable ester thereof.

9. A process for the preparation of a compound of the formula (I) as claimed in claim 1, which comprises of a) to i):

a) reacting a pyrimidine of formula (II):

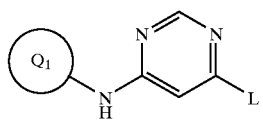

(II)

wherein L is a displaceable group, with a compound of formula (III):

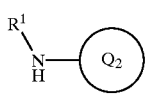

(III)

b) reaction of a pyrimidine of formula (IV):

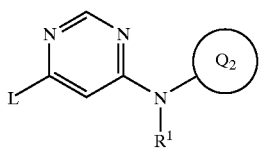

(IV)

wherein L is a displaceable group, with a compound of formula (V):

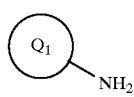

(V)

c) reacting a pyrimidine of formula (VI):

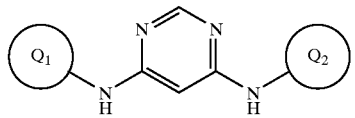

(VI)

with a compound of formula (VII)

$R^1$—L  (VII)

wherein L is a displaceable group;

d) for compounds of formula (I) where n=1, 2 or 3; m=1 and Y is OH, $NH_2$ or SH, reaction of a 3-membered heteroalkyl ring of formula (VIII):

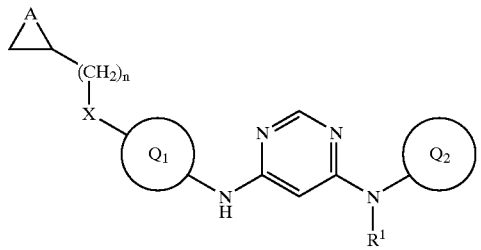

(VIII)

wherein A is O, S or NH;
with a nucleophile of formula (IX):

Z—D  (IX)

wherein D is H or a suitable counter-ion;

e) for compounds of formula (I) where X is oxygen, by reaction of an alcohol of formula (X)

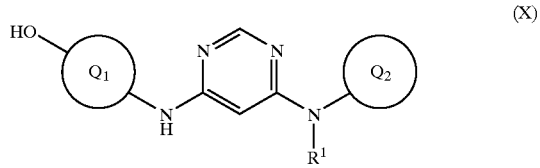

(X)

with an alcohol of formula (XI):

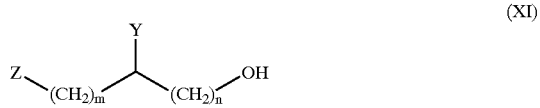

(XI)

f) for compounds of formula (I) wherein X is $CH_2$, O, NH or S; Y is OH and m is 2 or 3: reaction of a compound of formula (XII):

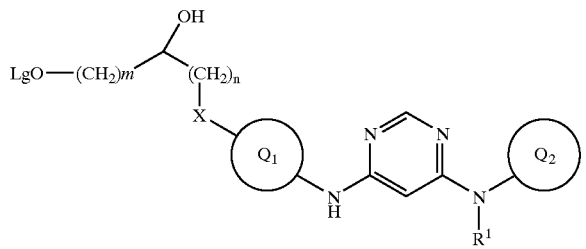

(XII)

wherein —OLg is a leaving group; with a nucleophile of formula Z—D (IX) wherein D is H or a suitable counter-ion;

g) for compounds of formula (I) wherein X is $CH_2$, O, NH or S; Y is H; n is 1, 2 or 3 and m is 1, 2 or 3: reaction of a compound of formula (XIII):

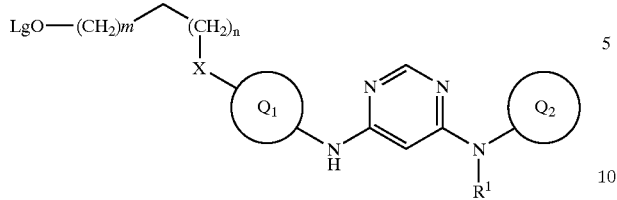

(XIII)

wherein —OLg is a leaving group; with a nucleophile of formula Z—D (IX) wherein D is H or a suitable counter-ion;

h) for compounds of formula (I) wherein X is O, NH or S; Y is H; n is 1, 2 or 3 and m is 1, 2 or 3: reaction of a compound of formula (XIV) with a compound of formula (XV):

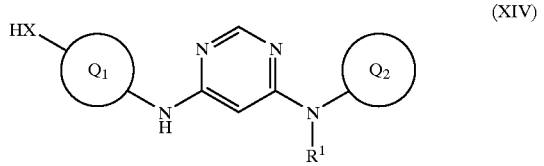

(XIV)

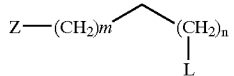

(XV)

or i) for compounds of formula (I) in which Z is SH, by conversion of a thioacetate group in a corresponding compound;

and thereafter if necessary:
(i) converting a compound of the formula (I) into another compound of the formula (I);
(ii) removing any protecting groups;
(iii) forming a pharmaceutically acceptable salt or in vivo hydrolysable ester; wherein L is a displaceable group and D is hydrogen or a counter-ion.

10. A pharmaceutical composition which comprises a compound of the formula (I) as claimed in any one of claims 1 to 8, or a pharmaceutically-acceptable salt or an in-vivo hydrolysable ester thereof, and a pharmaceutically-acceptable diluent or carrier.

11. A method for producing an anti-cancer effect in a warm blooded animal which comprises administering to said animal an effective amount of a compound of the formula (I) as claimed in any one of claims 1 to 8, or a pharmaceutically-acceptable salt, or in-vivo hydrolysable ester thereof.

* * * * *